(12) United States Patent
Crowley

(10) Patent No.: US 6,585,655 B2
(45) Date of Patent: *Jul. 1, 2003

(54) MEDICAL IMAGING DEVICE

(75) Inventor: Robert J. Crowley, Wayland, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/160,471

(22) Filed: May 31, 2002

(65) Prior Publication Data

US 2002/0188201 A1 Dec. 12, 2002

Related U.S. Application Data

(60) Division of application No. 10/039,419, filed on Jan. 4, 2002, which is a continuation of application No. 09/672,164, filed on Sep. 27, 2000, now Pat. No. 6,364,840, which is a continuation of application No. 08/938,342, filed on Sep. 26, 1997, now Pat. No. 6,165,127, which is a continuation of application No. 08/633,408, filed on Jun. 10, 1996, now Pat. No. 5,715,825, which is a continuation of application No. 08/442,818, filed on May 17, 1995, now Pat. No. 5,524,632, which is a division of application No. 08/253,629, filed on Jun. 3, 1994, now Pat. No. 5,421,338, which is a continuation of application No. 07/570,319, filed on Aug. 21, 1990, now abandoned, which is a continuation-in-part of application No. 07/171,039, filed on Mar. 21, 1988, now Pat. No. 4,951,677.

(51) Int. Cl.$^7$ .................................................. A61B 8/12

(52) U.S. Cl. ........................... 600/463; 600/471; 600/7

(58) Field of Search ................................. 600/437, 439, 600/461, 463, 466–467, 471, 566–567, 7; 606/108, 159, 167, 170–171, 180, 184–185

(56) References Cited

U.S. PATENT DOCUMENTS 1,167,014 A    1/1916   O'Brien (List continued on next page.)

FOREIGN PATENT DOCUMENTS

DE    3619195    2/1987
EP    0 139 574  2/1985

(List continued on next page.)

OTHER PUBLICATIONS

Alkoa Endo Scan Model 550–520.
Baba, K., "UTS Diagnostic Apparatus," EOC 0064275, published Nov. 24, 1982. (copy 128/662.060).
Bruel & Kjar, "Diagnostic Ultrasound for Advanced Applications".
Cole, "The Pulsed Doppler coronary Artery Catheter." *Circulation,* vol. 56, No. 1, Jul. 1977.
Hartley et al., "Pulsed Doppler Coronary Artery Catheter Transducers," *Cardiovascular Ultrasonic Flowmetry,* pp. 279–298, Altobelli, ed., Elsevier Science and Publishing Co., 1985.
Hisanaga, K., et al., "A New TE Real–Time Linear Scanner," *Proc. 23$^{rd}$ AIUM* 1978.
Kutz et al., "New Vein Stripper and Technique of Stripping," *Surgery,* 29:271–275, Feb. 1951.
Olympus GF–UM2/EU–MS.

(List continued on next page.)

*Primary Examiner*—Francis J. Jaworski
(74) *Attorney, Agent, or Firm*—Orrick, Herrington & Sutcliffe LLP

(57) ABSTRACT

A medical device for creating images of tissue within a body includes a disposable liquid-confining sheath supporting an elongate flexible drive shaft which carries an imaging device such as a ultrasound transducer. The device may include a trocar adapted to receive the sheath, the trocar permitting the device to be inserted into the body where no natural passageway exists, the trocar having a side-facing region adapted to maintain registry with the imaging device while the imaging device rotates. In another embodiment, the drive shaft includes an outer coil that is configured such that when the drive shaft is driven in the direction tending to decrease the diameter of the outer coil, the outer surface of the outer coil pressurizes liquid distally of the outer surface. The device optionally includes an inflatable balloon.

25 Claims, 19 Drawing Sheets

U.S. PATENT DOCUMENTS

| | | |
|---|---|---|
| 2,029,495 A | 2/1936 | Lowe |
| 2,545,101 A | 3/1951 | Meunier |
| 2,779,334 A | 1/1957 | Sandborn |
| 2,949,910 A | 8/1960 | Brown et al. |
| 3,256,733 A | 6/1966 | Carlin |
| 3,542,014 A | 11/1970 | Peronneau |
| 3,547,101 A | 12/1970 | Rosauer |
| 3,614,953 A | 10/1971 | Moss |
| 3,699,964 A | 10/1972 | Ericson ............... 128/275 |
| 3,704,711 A | 12/1972 | Park |
| 3,749,085 A | 7/1973 | Wilson et al. |
| 3,749,086 A | 7/1973 | Kline et al. |
| 3,762,416 A | 10/1973 | Moss et al. |
| 3,773,034 A | 11/1973 | Burns et al. |
| 3,779,234 A | 12/1973 | Eggleton et al. |
| 3,817,089 A | 6/1974 | Eggleton et al. |
| 3,834,392 A | 9/1974 | Lampman et al. ..... 128/303.13 |
| 3,837,345 A | 9/1974 | Matar |
| 3,938,502 A | 2/1976 | Bom |
| 3,942,530 A | 3/1976 | Northeved ............ 128/303.15 |
| 4,011,869 A | 3/1977 | Seiler, Jr. |
| 4,020,829 A | 5/1977 | Willson et al. |
| 4,020,847 A | 5/1977 | Clark, III |
| 4,137,920 A | 2/1979 | Bonnet |
| 4,176,662 A | 12/1979 | Frazer |
| 4,273,128 A | 6/1981 | Lary |
| 4,275,597 A | 6/1981 | Quedens et al. |
| 4,290,427 A | 9/1981 | Chin |
| 4,319,580 A | 3/1982 | Colley et al. |
| 4,325,381 A | 4/1982 | Glenn ............... 128/660.1 |
| 4,327,738 A | 5/1982 | Green et al. |
| 4,354,500 A | 10/1982 | Colley et al. |
| 4,354,501 A | 10/1982 | Colley et al. |
| 4,374,525 A | 2/1983 | Baba ............... 128/660 |
| 4,375,818 A | 3/1983 | Suwaki et al. |
| 4,391,282 A | 7/1983 | Andou et al. |
| 4,402,308 A | 9/1983 | Scott |
| 4,431,006 A | 2/1984 | Trimmer et al. |
| 4,462,408 A | 7/1984 | Silverstein |
| 4,466,443 A | 8/1984 | Utsugi |
| 4,466,444 A | 8/1984 | Baba |
| 4,475,553 A | 10/1984 | Yamaguchi et al. |
| 4,489,727 A * | 12/1984 | Matsuo et al. ............... 600/463 |
| 4,494,549 A | 1/1985 | Namba et al. |
| 4,516,972 A | 5/1985 | Samson |
| 4,546,771 A | 10/1985 | Eggleton et al. ............ 128/660 |
| 4,558,706 A | 12/1985 | Nakada |
| 4,572,201 A | 2/1986 | Kondo et al. |
| 4,576,177 A | 3/1986 | Webster, Jr. |
| 4,589,419 A | 5/1986 | Laughlin et al. ....... 128/660.03 |
| 4,605,009 A | 8/1986 | Pourcelot et al. |
| 4,633,882 A | 1/1987 | Matsuo et al. |
| 4,669,465 A | 6/1987 | Moore et al. ............ 128/303.1 |
| 4,674,515 A | 6/1987 | Andou et al. |
| 4,729,384 A | 3/1988 | Bazenet |
| 4,732,156 A | 3/1988 | Nakamura |
| 4,754,752 A | 7/1988 | Ginsburg et al. ...... 128/303.12 |
| 4,771,788 A | 9/1988 | Miller |
| 4,794,931 A | 1/1989 | Yock ............... 128/660.03 |
| 4,802,487 A | 2/1989 | Martin et al. ............... 600/463 |
| 4,821,731 A | 4/1989 | Martinelli et al. ..... 128/662.05 |
| 4,841,977 A | 6/1989 | Griffith et al. ......... 128/660.03 |
| 4,887,606 A | 12/1989 | Yock et al. ............ 128/662.05 |
| 4,889,128 A | 12/1989 | Millar ................... 128/662.06 |
| 4,899,757 A | 2/1990 | Pope, Jr. et al. ........ 128/662.06 |
| 4,911,170 A | 3/1990 | Thomas, III et al. |
| 4,917,097 A | 4/1990 | Proudian et al. ....... 128/662.06 |
| 4,936,307 A | 6/1990 | Saito et al. |
| 4,951,677 A * | 8/1990 | Crowley et al. ............ 600/463 |
| 4,955,377 A | 9/1990 | Lennox et al. ............. 128/401 |
| 4,979,939 A | 12/1990 | Shiber ....................... 606/159 |
| 4,991,588 A | 2/1991 | Pfueger et al. ........ 128/662.06 |
| 5,000,185 A | 3/1991 | Yock ..................... 128/662.03 |
| 5,002,059 A | 3/1991 | Crowley et al. ....... 128/662.06 |
| 5,024,234 A | 6/1991 | Leary et al. ........... 128/663.01 |
| 5,029,588 A | 7/1991 | Yock et al. ............ 128/662.06 |
| 5,040,548 A | 8/1991 | Yock ......................... 128/898 |
| 5,049,130 A | 9/1991 | Powell ....................... 604/96 |
| 5,061,273 A | 10/1991 | Yock ......................... 606/194 |
| 5,095,911 A | 3/1992 | Pomeranz ............. 128/662.06 |
| 5,100,424 A | 3/1992 | Jang et al. .................. 606/159 |
| 5,105,819 A | 4/1992 | Wollschlager et al. |
| 5,117,831 A | 6/1992 | Jang et al. .................. 606/159 |
| 5,524,630 A * | 6/1996 | Crowley ..................... 600/466 |
| 6,364,840 B1 * | 4/2002 | Crowley ..................... 600/463 |

FOREIGN PATENT DOCUMENTS

| | | |
|---|---|---|
| EP | 0 163 502 | 4/1985 |
| EP | 0 251 745 A1 | 7/1988 |
| FR | 2 424 733 | 5/1978 |
| FR | 2 584 288 | 1/1987 |
| GB | 2 044 103 A | 10/1980 |
| GB | 2 157 828 A | 10/1985 |
| WO | WO 83/01893 | 6/1983 |
| WO | WO 83/04174 | 12/1983 |
| WO | WO 89/12425 | 12/1989 |
| WO | WO 90/02520 | 3/1990 |
| WO | WO 91/03207 | 3/1990 |
| WO | WO 91/14401 | 10/1991 |
| WO | WO 92/00710 | 1/1992 |

OTHER PUBLICATIONS

Holm et al., "Transurethral and Transrectal Ultrasonic Scanning," date unknown.

Holm et al., "A Transurethral Ultrasonic Scanner," 1973.

Holm et al., Ultrasonically guided Precise Needle Placement in the prostate and the Seminal Vesicles, 1981.

S.S. White Industrial Products brochure.

Samuels et al., "In situ Saphenous Vein Arterial Bypass: A Study of the Anatomy Pertinent to Its Use In Situ As a Bypass Graft with a Description of a New Venous Valvulotme," *Amer. Surgeon*, 34:120–130, Feb. 1968.

Skagset et al., "In situ Vein Bypass: Experience with New Vein Valve Strippers," *Scand. J. Thor*.

Takahashi et al., "The Ultrasonic Diagnosis in the Field of Urology (The $2^{nd}$ Report)—On the Diagnosis of Prostate Disease—".

Martin et al., "Design Characteristics for Ultrasonic Catheters," *international Journal of Cardiac Imaging 4*, pp. 201–216, 1989.

Gammelgaard and Holm, "Transurethral and Transrectal Ultrasonic Scanning in Urology," *The Journal of Urology*, vol. 124, 1980.

* cited by examiner

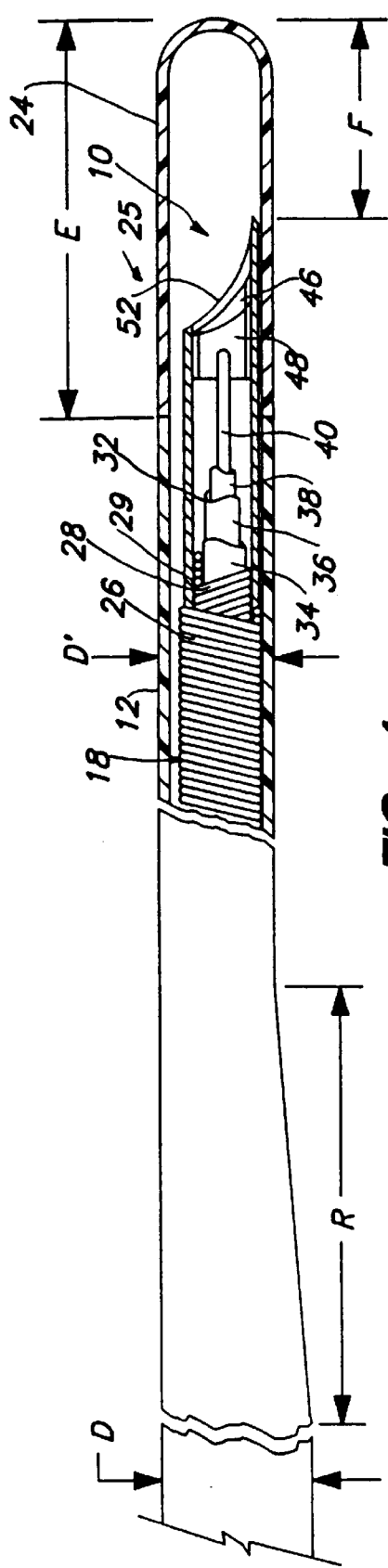
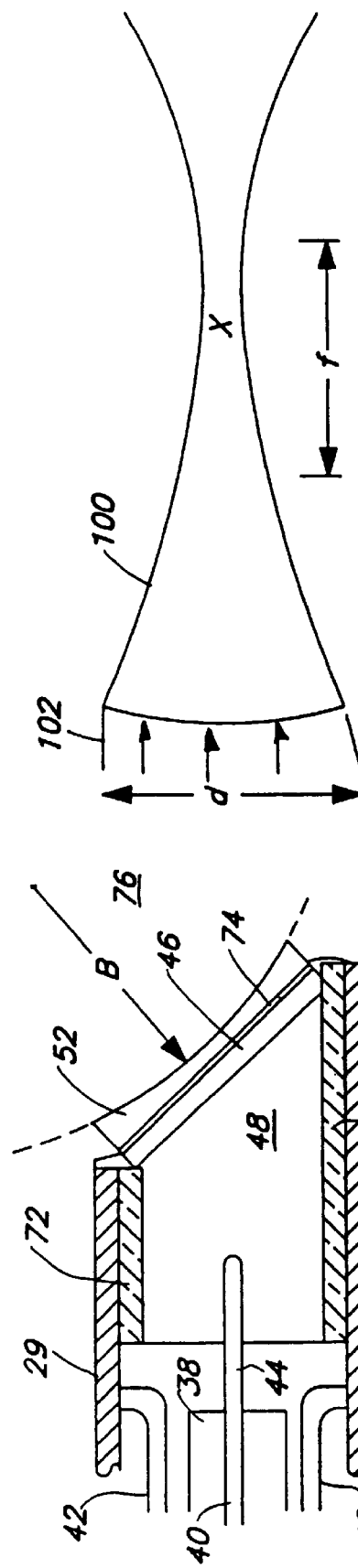
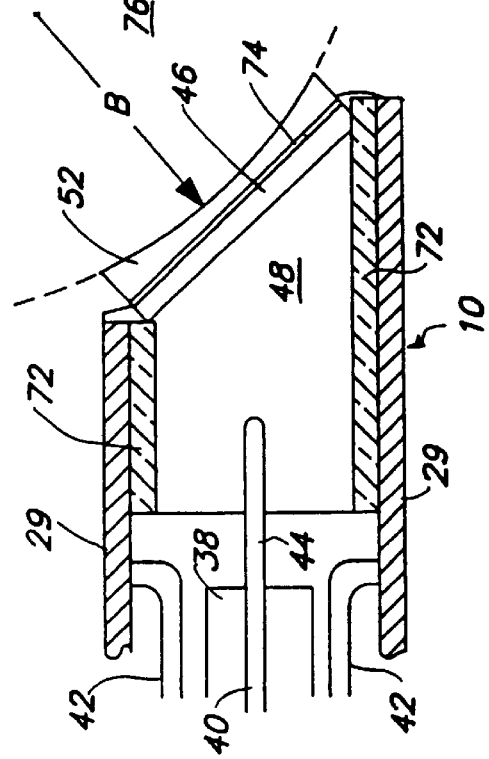
FIG. 4
FIG. 5
FIG. 6

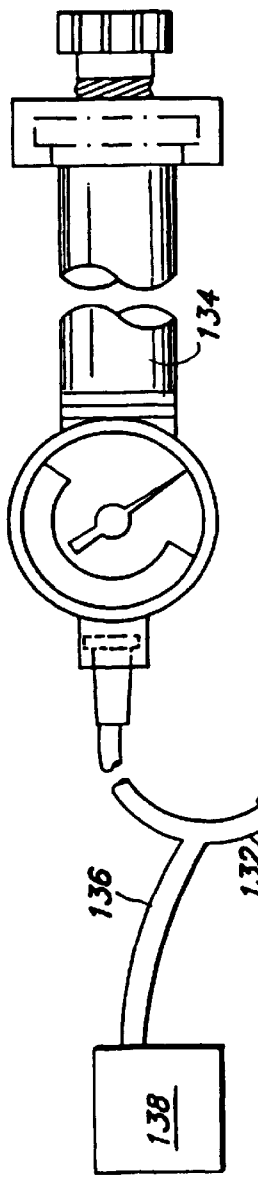
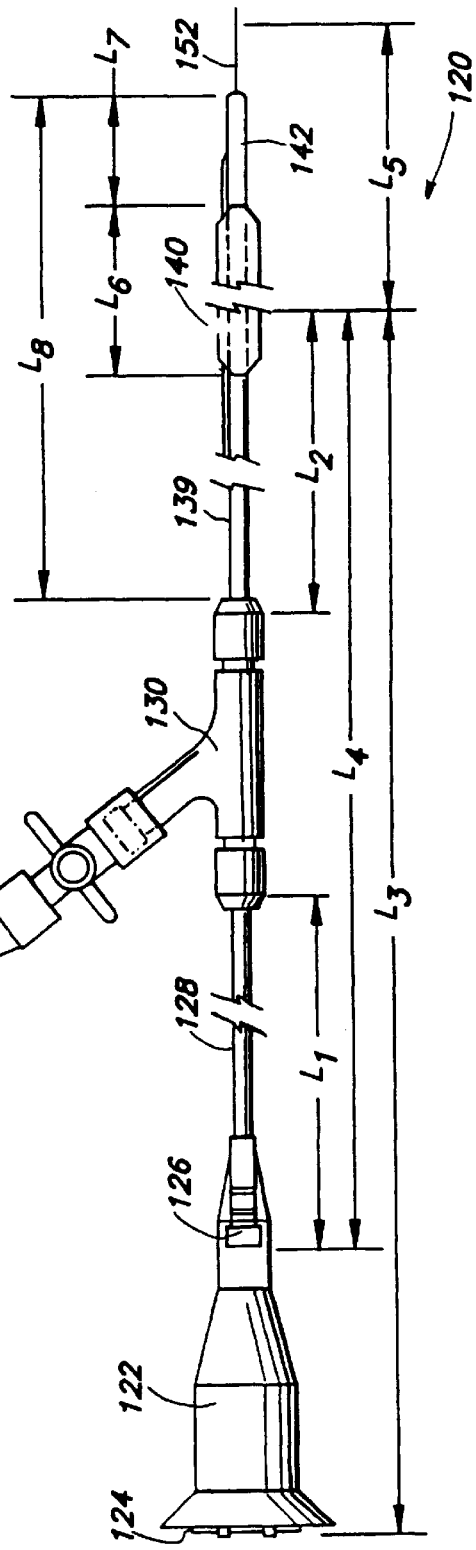
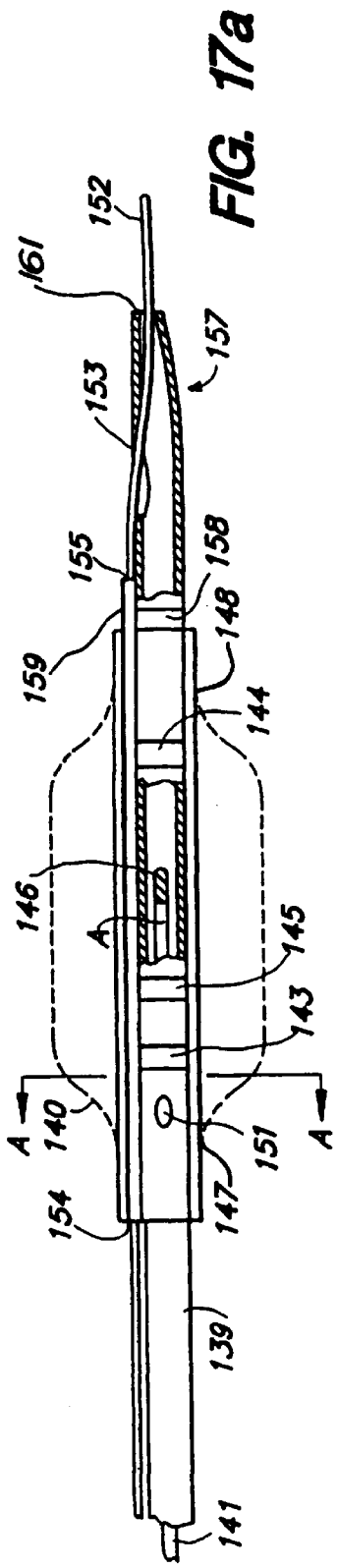
FIG. 17
FIG. 17a

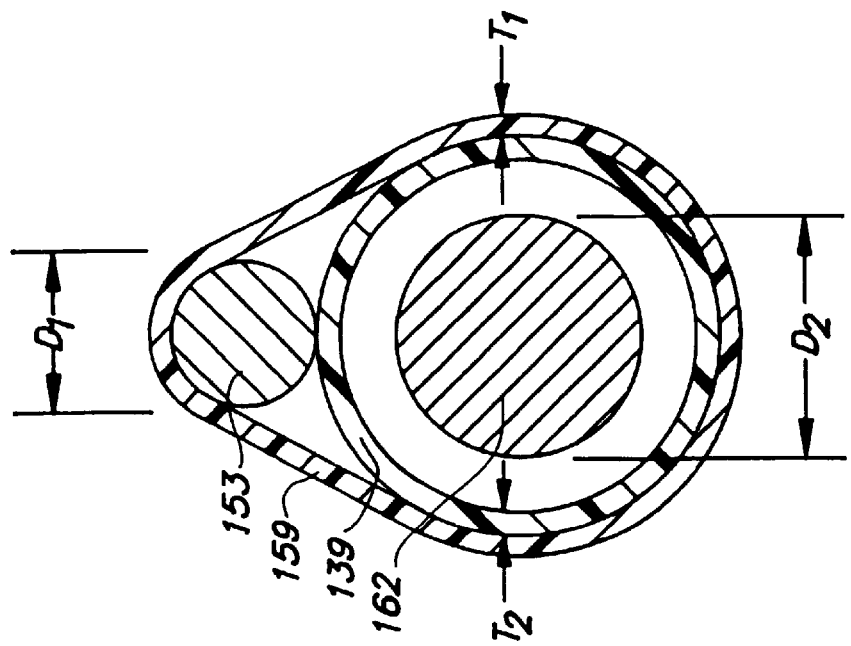
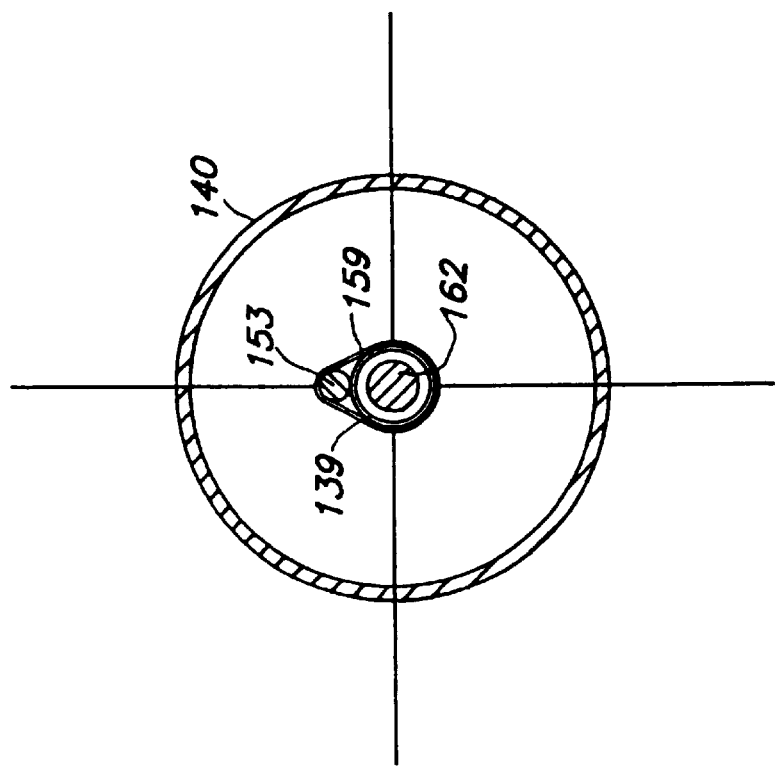

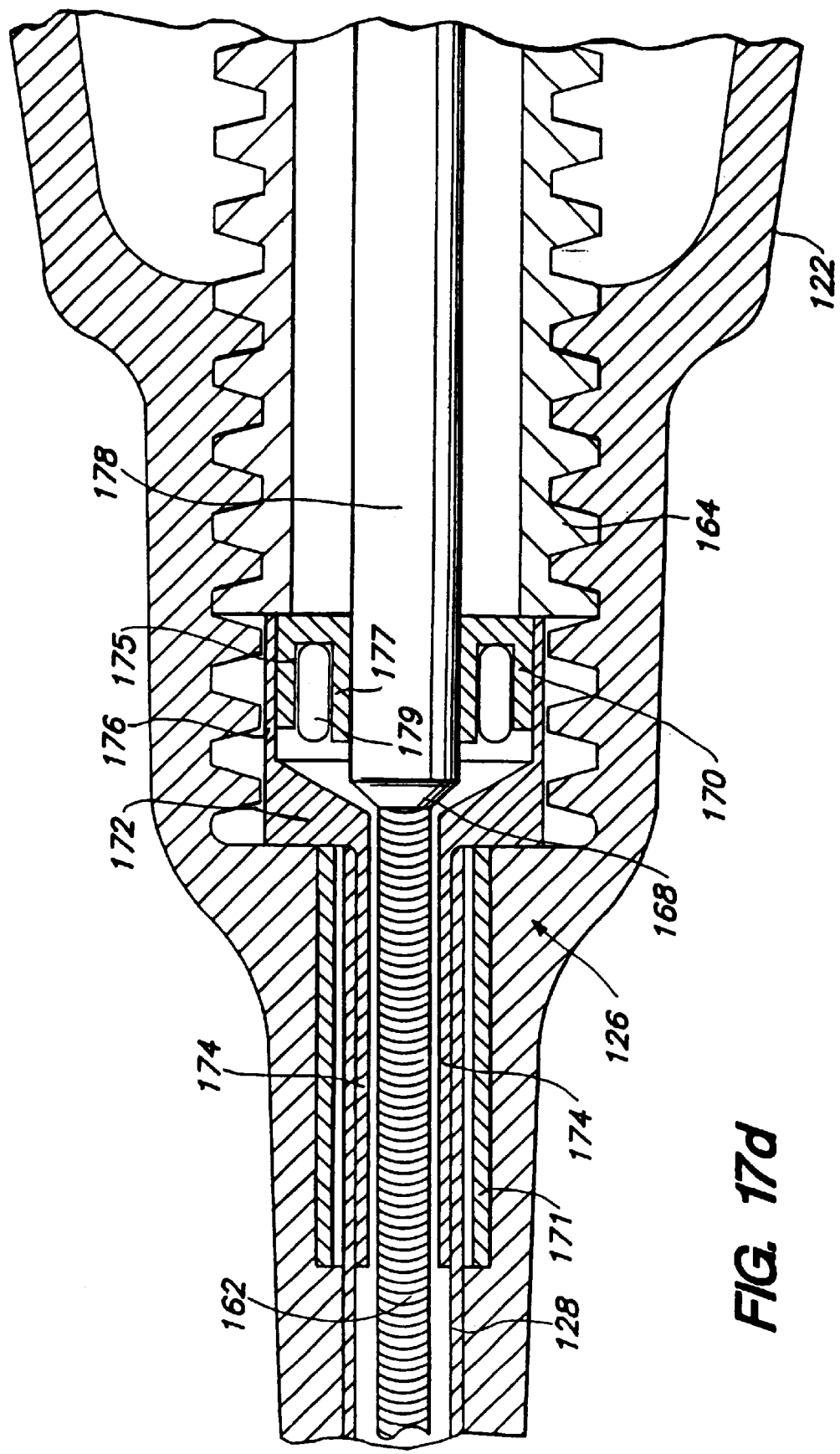

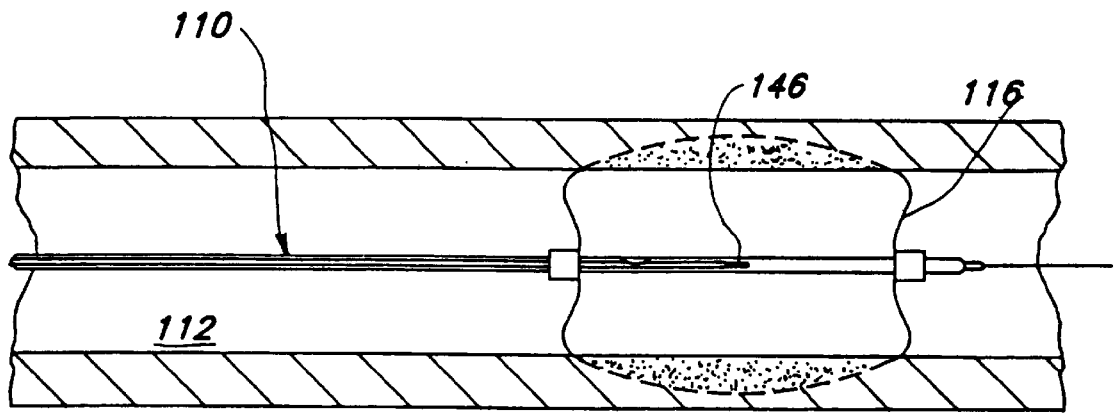
FIG. 18d
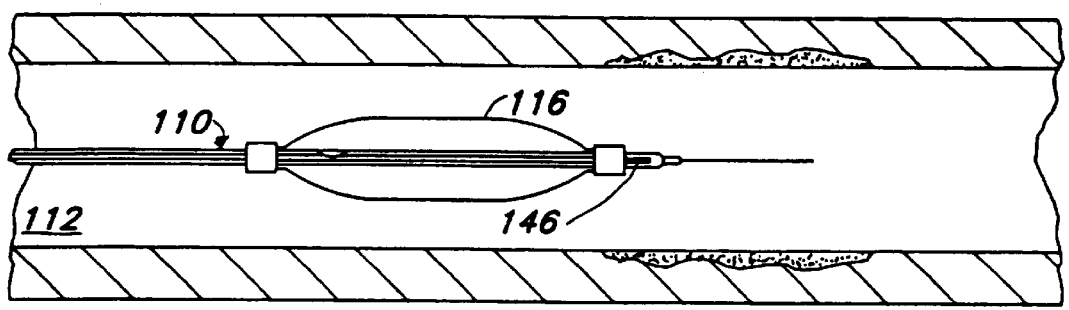
FIG. 18e
FIG. 19
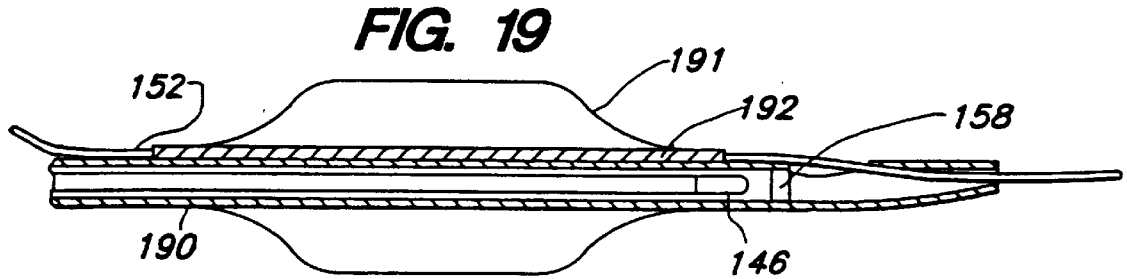
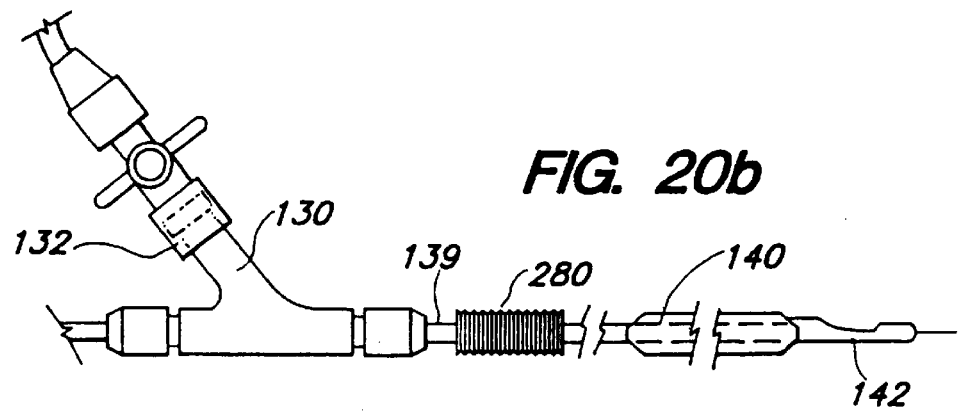
FIG. 20b

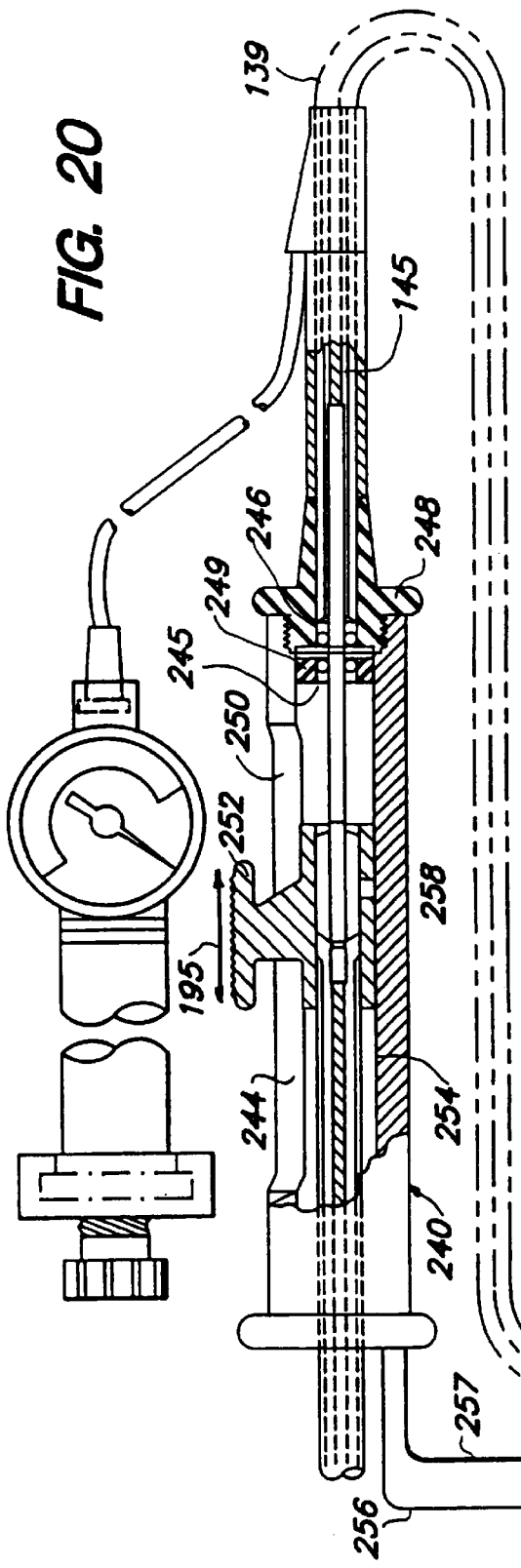
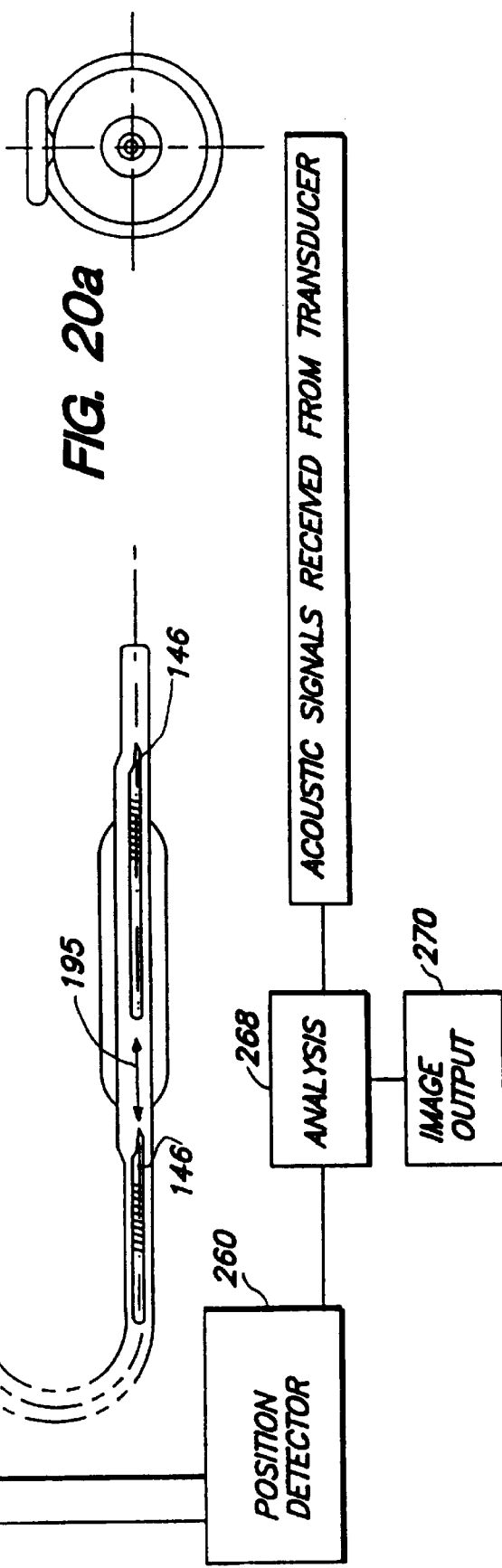

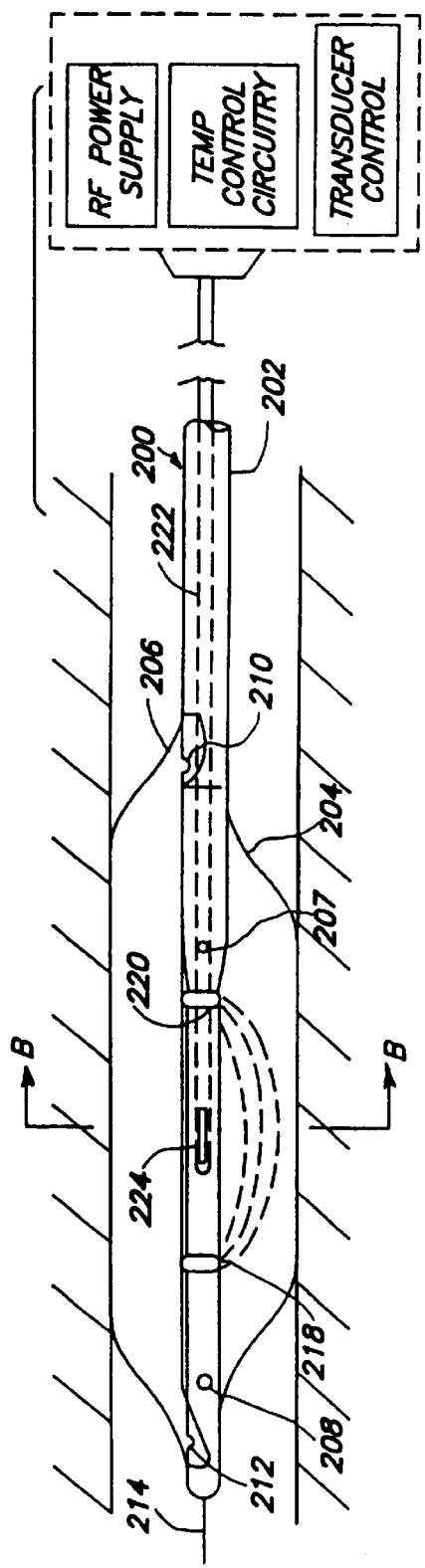
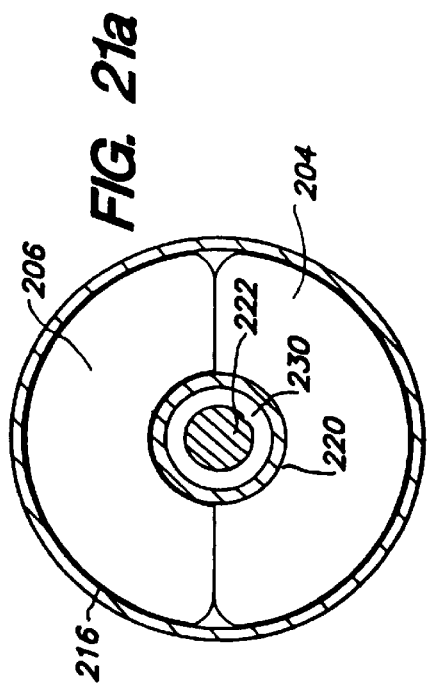
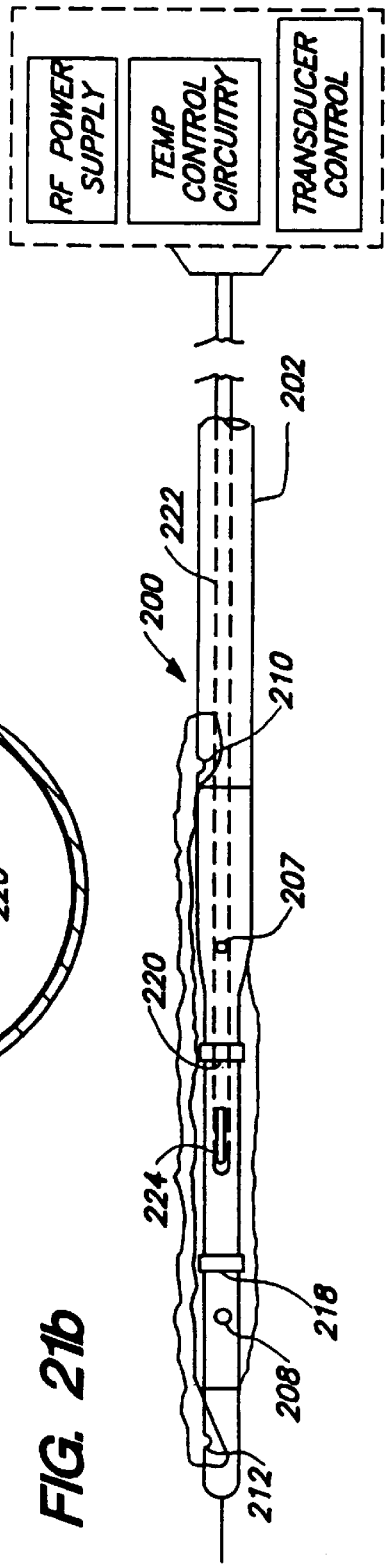
FIG. 21
FIG. 21a
FIG. 21b

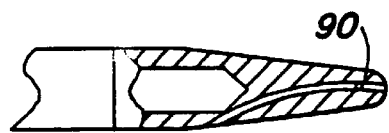
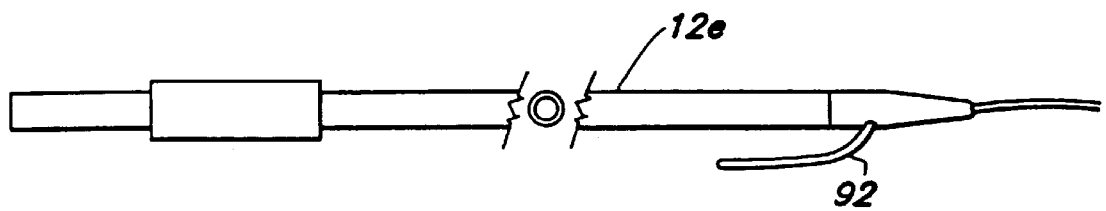
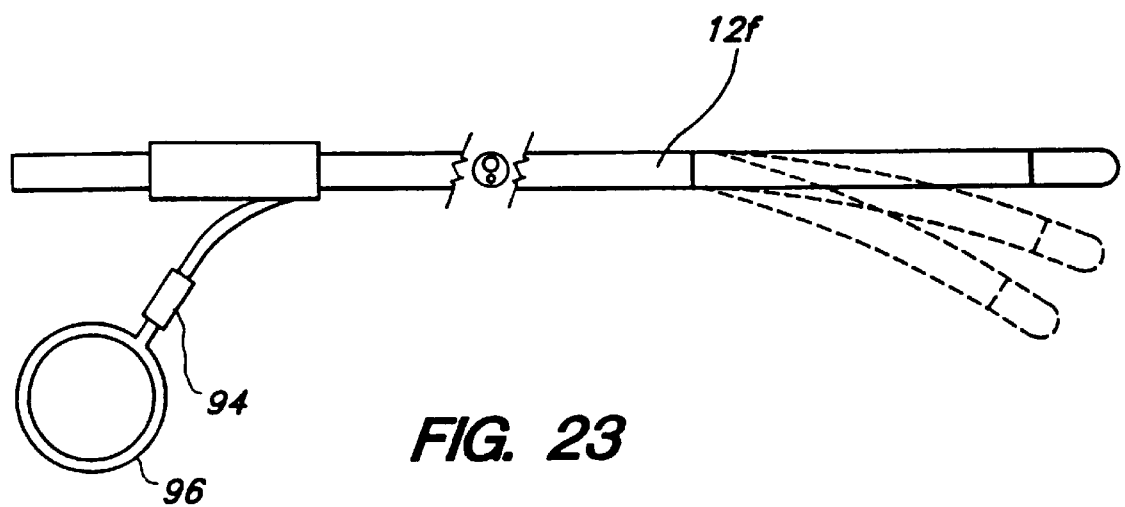

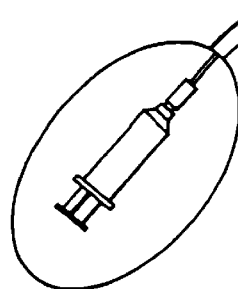
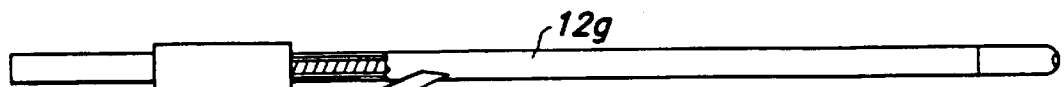
FIG. 24
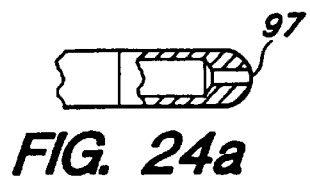
FIG. 24a
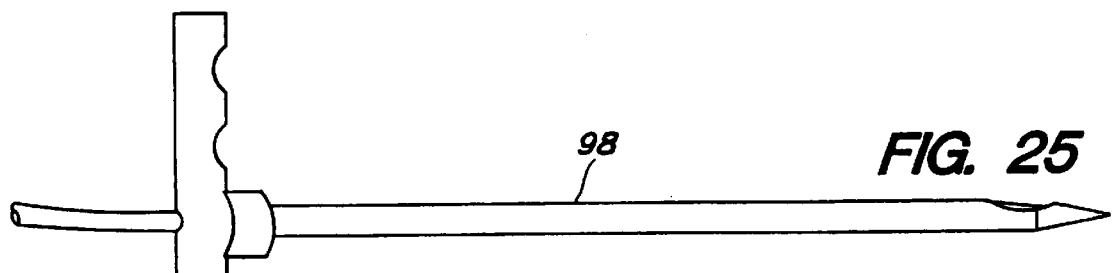
FIG. 25
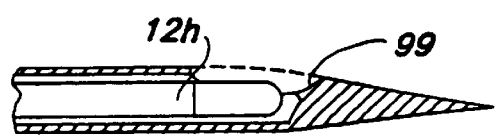
FIG. 25a
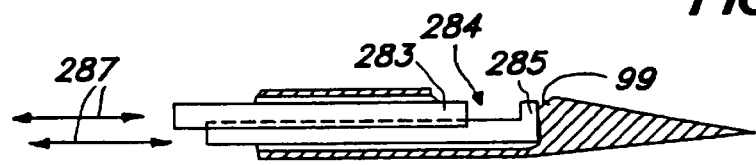
FIG. 25b
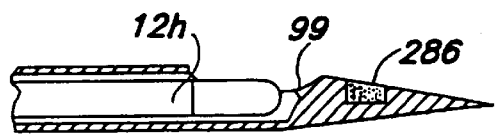
FIG. 25c
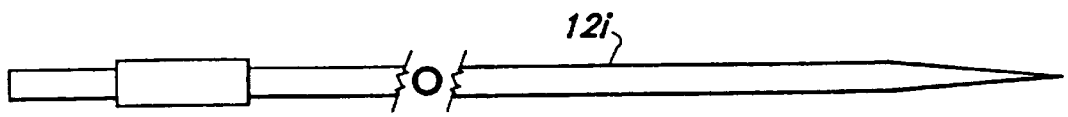
FIG. 26
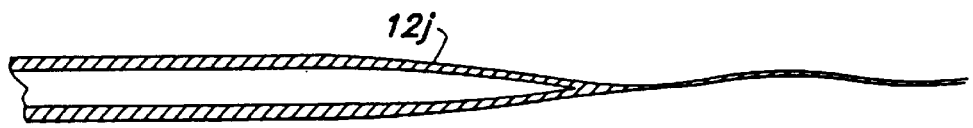
FIG. 27

MEDICAL IMAGING DEVICE

CROSS-REFERENCE TO RELATED APPLICATIONS

The is a divisional application under 37 CFR §1.53(b) of prior application Ser. No. 10/039.419 filed on Jan. 4. 2002, which is a continuation of patent application, U.S. Ser. No. 09/672,164, filed Sep. 27, 2000, now U.S. Pat. No. 6,364,840 which is a continuation of Ser. No. 08/938,342, filed on Sep. 26, 1997, now U.S. Pat. No. 6,165,127, which is a continuation of Ser. No. 08/633,408, filed on Jun. 10, 1996, which issued as U.S. Pat. No. 5,715,825, which is a continuation of Ser. No. 08/442,818, filed on May 17, 1995, which issued as U.S. Pat. No. 5,524,630, which is a divisional of Ser. No. 08/253,629, filed on Jun. 3, 1994, which issued as U.S. Pat. No. 5,421,338, which is a continuation of Ser. No. 07/570,319, filed on Aug. 21, 1990, abandoned, which is a continuation-in-part of Ser. No. 07/171,039, filed on Mar. 21, 1988, which issued as U.S. Pat. No. 4,951,677. The priority of these prior applications is expressly claimed and their disclosures are hereby incorporated by reference in their entirety.

BACKGROUND OF THE INVENTION

Background

This invention relates to acoustic imaging catheters employing a rotating transducer.

It has long been recognized that acoustic imaging by use of internal probes has potential use in visualizing conditions of a body.

Wider effective use of acoustic imaging would occur, especially in the vascular system, if such a system could be considerably smaller, have good image fidelity, and be simple, inexpensive and dependable.

SUMMARY OF THE INVENTION

In a first aspect, the invention features an acoustic imaging catheter device, that has a flexible, axially elongated ultrasonic probe formed of a rotatable drive shaft with an ultrasonic transducer at its distal end, a catheter body in the form of an elongated, resinous, flexible member, and an inflatable balloon disposed on the catheter body, the catheter body having a distal portion extending distally beyond the balloon, the material of the balloon, the portion of the catheter body carrying the balloon and the distal portion of the catheter body beyond the balloon are sonolucent and substantially matched in acoustic impedance with fluid to which the catheter is exposed. A probe receiving passage within the catheter body is constructed and arranged to rotatably slidably support the elongated ultrasonic probe at rotational speed enabling generation of acoustic images. The catheter body and flexible ultrasonic probe are cooperatively constructed and arranged to enable axial sliding motion of the probe within the catheter body to position the transducer between at least two positions, one position located in the distal portion of the catheter, distal to the balloon, for providing an image of the wall of a body lumen in which the device is inserted to locate a region of the lumen wall requiring treatment or for viewing the lumen wall after treatment, and the other position located in the region of the catheter corresponding to the balloon, enabling viewing of the lumen wall while the balloon applies treatment conditions to the lumen wall.

In various preferred embodiments, the transducer is variably positionable in the catheter along the length of the balloon. The transducer is also positionable in a region of the catheter proximal to the balloon, the proximal region of the catheter body being sonolucent and substantially matched in acoustic impedance with fluid to which the catheter is exposed. The transducer is variably positionable from a region of the catheter proximal to the balloon, to a region distal to the balloon.

In various preferred embodiments, the catheter device includes a position detector means adapted to detect the axial position of the transducer within the catheter body and processing means to provide an image of the body lumen as a function of the axial position and acoustic image information obtained during rotation of the transducer. The processing means includes storage means to store acoustic image information from selected axial positions of the catheter body and image reconstruction means to provide therefrom a three-dimensional image of the body lumen. The processing means is constructed and arranged to provide a three-dimensional image of the body lumen corresponding to a range of axial travel of the transducer in the catheter.

In another aspect, the invention features an acoustic imaging catheter device capable of treatment of a body lumen having a flexible axially elongated ultrasonic probe comprising a rotatable drive shaft with an ultrasonic transducer at its distal end, a catheter body in the form of an elongated, resinous, flexible member, and an inflatable treatment balloon constructed and arranged on the catheter to apply a therapeutic treatment to a portion of the human body which the balloon contacts. The material of the balloon, and the portion of the catheter body carrying the balloon are sonolucent and substantially matched in acoustic impedance with fluid to which the catheter is exposed. A probe receiving passage within the catheter body is constructed and arranged to rotatably slidably support the elongated ultrasonic probe at rotational speed enabling generation of acoustic images. The transducer has a position within the catheter at the location of the balloon, and is arranged to form acoustic images of the portion of the body contacted by the treatment balloon during the progress of the treatment.

In various preferred embodiments, the treatment balloon is an inflatable dilatation balloon disposed on the catheter body, the wall of the balloon being comprised of non-elastomeric material resistant to substantial stretching under the dilatation pressure. The treatment balloon is associated with heating means heating inflation liquid within the balloon to controlled treatment temperature. The heating means includes electrodes connectable to a radio frequency energy source capable of heating electrically conductive liquid in the balloon on the basis of I2R losses. The catheter body has a single probe-receiving lumen constructed and arranged to slidably receive and support the elongated ultrasonic probe in a rotatable manner. The probe-receiving lumen is constructed to convey inflation fluid from a dilatation pressure source to the interior of the balloon to inflate the balloon to dilatation pressure. The catheter body and flexible ultrasonic probe are cooperatively constructed and arranged to enable positioning of the transducer in a region of the catheter axially corresponding to the balloon for observing a region of the body simultaneously while treatment thereof is being performed by the balloon. The catheter body has a distal portion extending distally from the balloon. The distal portion of the catheter body being sonolucent and substantially matched in acoustic impedance with fluid to which the catheter is exposed, and the catheter body and flexible ultrasonic probe cooperatively constructed and arranged to enable axial sliding motion of the probe within the catheter body to position the transducer between at least two positions, one position located at the distal portion of the catheter, distal to the balloon, for providing an image of the wall of a body lumen in which the device is inserted to locate a region of the lumen wall requiring treatment or for viewing the lumen wall requiring treatment or for viewing the lumen wall after treatment and the other position located in the region of the catheter corresponding to the balloon, enabling viewing tissue while the balloon applies treatment conditions to the lumen wall.

In various preferred embodiments, the device further includes an inflation means comprising a screw syringe for generating dilatation pressures in the balloon. The catheter body extends through the full length of the balloon and includes a fluid port in the region of the balloon for inflating the balloon and equalization of pressure in the balloon and the catheter body. The sonolucent portion of the catheter body has a wall thickness of about 0.010 inch or less.

In various preferred embodiments, the device includes further a saddle member of limited axial extent fixed to the exterior of a portion of the catheter body corresponding to the location of the balloon. The saddle includes a lumen enabling passage of a guidewire along the exterior of the catheter body through the balloon, with portions of the guidewire proximal and distal of the balloon being exposed to the body lumen. The distal catheter extension includes a first aperture in the side wall and a second aperture, axially arranged in the distal end of the extension and the guidewire is threaded through the first and second apertures to extend distally from the device. The tubular saddle member is sonolucent and substantially matched in acoustic impedance with fluid to which the catheter is exposed. The tubular member is formed of polyethylene.

In various preferred embodiments, the device includes a sealing member at the proximal portion of the catheter apparatus including a low friction seal in contact with the drive shaft for preventing flow of inflation fluids to distal portions of the drive shaft at dilatation pressures, while enabling rotation thereof. The drive shaft and sealing member are cooperatively constructed to enable axial motion of the transducer with respect to the catheter sheath. The sealing member includes a ball seal contacting a portion of the drive shaft and enabling rotation thereof while preventing flow of inflation fluids proximal to the ball seal. The balloon is formed of polyethylene.

In various preferred embodiments the device is sized and constructed for treatment in the vascular system. The device is sized and constructed for balloon angioplasty. The device is sized and constructed for treatment in the esophagus. The device is sized and constructed for treatment in the prostate.

In various preferred embodiments, the device further includes a self-sealing septum enabling venting of the catheter body. The septum is adapted for venting inflation fluid, provided to the catheter body in excess to prepare the catheter for use. The septum is adapted for venting air, when inflation fluid is provided to the catheter body in excess to prepare the catheter for use.

In various preferred embodiments, the entire length of the catheter body is sonolucent. The device includes means for asymmetric treatment of the vessel. The means for asymmetric treatment includes means for asymmetric heating. The asymmetric means includes multiple balloons arranged to provide asymmetric heating. The means includes an asymmetric balloon. The catheter body includes a bellows enabling extension and retraction of the body with respect to the transducer.

In another aspect, the invention also features an acoustic imaging catheter device having a flexible elongated ultrasonic probe comprising a rotatable drive shaft with an ultrasonic transducer at its distal end, a catheter body in the form of an elongated, resinous, flexible member, and an inflatable balloon disposed on the catheter body, the catheter body has a distal portion extending distally from the balloon. The distal portion of the catheter body is sonolucent and substantially matched in acoustic impedance with fluid to which the catheter is exposed, and a passage within the catheter body is constructed and arranged to slidably receive and support the elongated ultrasonic probe in a rotatable manner. The catheter body and flexible ultrasonic probe are cooperatively constructed and arranged to position the probe within the catheter body to position the transducer in the sonolucent catheter extension for providing an image of the wall of a body lumen in which the device is inserted, to locate a region of the lumen wall requiring treatment or for viewing the lumen wall after treatment.

In another aspect, the invention features an acoustic imaging dilatation device having a flexible elongated ultrasonic probe comprising a rotatable drive shaft with an ultrasonic transducer at its distal end, a catheter body in the form of an elongated, resinous, flexible member capable of withstanding dilatation pressures of 100 psi or more, and an inflatable balloon disposed on the catheter body, inflatable to the dilatation pressure, and being comprised of non-elastomeric material resistant to substantial stretching under the dilatation pressure. A distal portion of the catheter body in the vicinity of the balloon is sonolucent and substantially matched in acoustic impedance with fluid to which the catheter is exposed, and a passage within the catheter body is constructed and arranged to receive and support the elongated ultrasonic probe in a rotatable manner. The catheter body and flexible ultrasonic probe are cooperatively constructed and arranged to position the probe within the catheter body to position the transducer in the sonolucent catheter portion for providing an image of the wall of a body lumen in which the device is inserted.

In various preferred embodiments, the catheter body is a single lumen catheter body adapted to receive the probe and connected to a source of dilatation pressure for inflation of the balloon. The sonolucent portion of the catheter body corresponds with the location of the balloon. The sonolucent portion is a distal extension of the catheter, distal to the balloon. The catheter body extends the length of the balloon and includes a fluid port in the region of the balloon for inflation of the balloon and equalization of pressure in the balloon and catheter body.

In various embodiments, the catheter body has a distal portion extending distally from the balloon. The distal portion of the catheter body is sonolucent and substantially matched in acoustic impedance with fluid to which the catheter is exposed, and the catheter body and flexible ultrasonic probe are cooperatively constructed and arranged to enable axial sliding motion of the probe within the catheter body to position the transducer between at least two positions. One position is located at the distal portion of the catheter, distal to the balloon, for providing an image of the wall of a body lumen in which the device is inserted to locate a region of the lumen wall requiring treatment or for viewing the lumen wall after treatment, and the other position is located in the region of the catheter corresponding to the balloon, enabling viewing of the lumen wall while the balloon applies treatment conditions to the lumen wall.

In another aspect, the invention features an acoustic imaging catheter device having a closed, continuous catheter body in the form of an elongated, resinous, flexible member containing therein a pressurized fluid. At least the distal portion of the catheter body is sonolucent and substantially matched in acoustic impedance with fluid to which the catheter is exposed. A flexible elongated ultrasonic probe is provided comprising a rotatable drive shaft with an ultrasonic transducer at its distal end. The transducer has an outer diameter corresponding to the outer diameter of the drive shaft and mounted coaxially therewith. The drive shaft and transducer head forming a core that can be slidably inserted via the proximal end into the tubular body having a closed distal end to a directly, rotatably supported relationship with the body and after use can be slidably removed from the catheter body for repeated re-use in other catheter bodies. A sealing member is provided at the proximal portion of the catheter apparatus including a low friction seal in contact with the drive shaft for preventing flow of fluids to distal portions of the drive shaft, while enabling rotation thereof. The catheter body, sealing member and flexible ultrasonic probe are cooperatively constructed and arranged to enable axial sliding motion of the probe within the catheter body to position the transducer between positions in the acoustically transparent regions of the catheter body sheath for providing an image of the wall of a body lumen to locate a region requiring treatment. In pictured embodiments, a medical device is actuatable by the pressurized fluid.

In another aspect, the invention features a method for balloon dilatation. The method includes providing a balloon dilatation acoustic imaging device including a flexible elongated ultrasonic probe comprising a rotatable 25 drive shaft with an ultra-sonic transducer at its distal end, a catheter body in the form of an elongated, resinous, flexible member capable of withstanding dilatation pressures of about 100 psi or more, and an inflatable balloon disposed on the catheter body. The material of the balloon and a portion of the catheter body are sonolucent and substantially matched in acoustic impedance with fluid to which the catheter is exposed. A passage within the catheter body is constructed and arranged to receive and support the elongated ultrasonic probe in a rotatable manner. The catheter and flexible ultrasonic probe are cooperatively constructed to position the transducer in the sonolucent portion of the catheter. While viewing images from the transducer, the catheter body is introduced to a body lumen having a region to be dilated, and advanced in the lumen to the region to be dilated and positioning the balloon about the region. The region is treated by balloon dilatation, and the balloon deflated. The treated region is observed to determine further treatment, and the device is removed from the body lumen.

In various preferred embodiments, the catheter body includes a distal portion extending distally from the balloon and the method includes positioning the transducer in the distal portion. The catheter balloon and the catheter body portion carrying the balloon are sonolucent, and the catheter body and flexible ultrasonic probe are cooperatively constructed and arranged to enable axial sliding motion of the probe within the catheter body to position the transducer between at least two positions, one position located in the region of the catheter corresponding to the balloon and another position located in the distal portion of the catheter, distal to the balloon, for providing an image of the wall of a body lumen in which the device is inserted to locate a region of the lumen wall requiring treatment. The probe is slid to the position distal to the balloon while advancing the catheter body to the region to be dilated, and the probe is slid to the position corresponding to the balloon during dilatation. The probe is slid to the position corresponding to the distal region after dilatation for observing the treated body lumen.

In various preferred embodiments, the balloon is constructed to enable asymmetric treatment of the body lumen and the method includes torquing the catheter body while viewing acoustic images of the lumen to properly position the balloon to effect the asymmetric treatment to a desired portion of the lumen. The apparatus further includes a self-sealing septum and the method further includes preparing the apparatus by substantially removing air from the balloon and catheter sheath. The preparing includes removing air by flushing excess fluid through the septum. The preparing includes removing air by aspirating through the septum.

In another aspect, the invention features an apparatus for detection of cancerous tumors in tissue having no natural passageway, having an elongated ultrasonic probe comprising a transducer supported on the end of an elongated rotatable drive shaft in combination with a hollow trocar adapted to receive the probe, the trocar having a side-facing sonolucent region adapted to register with the transducer while rotating, enabling the transducer to form acoustic images of tissue into which the trocar has been forced.

In various preferred embodiments, the transducer is removable from the trocar and the apparatus further includes a biopsy sampling device positionable in the trocar to sample tissue. The sampling device is a forceps. The device includes a radioactive pellet for radiation treatment of a tumor found by ultrasonic imaging.

In yet another aspect, the invention features a method for detection of cancerous tumors in tissue having no natural passageway. An elongated ultrasonic probe is provided comprising a transducer supported on the end of an elongated rotatable drive shaft in combination with a hollow trocar adapted to receive the probe, the trocar having a side-facing sonolucent region adapted to register with the transducer while rotating, enabling the transducer to form acoustic images of tissue into which the trocar has been forced, and, while observing ultrasonic images from the probe, advancing the probe into the tissue.

In preferred embodiments the probe is removable from the trocar, and the method further comprises, at the position of a tumor removing the transducer from the trocar, and introducing to the trocar a biopsy sampling means of sampling the tumor. The biopsy sampling means is a forceps. The tissue is the liver. The tissue is the breast.

According to another aspect of the invention, an elongated, flexible ultra-sonic probe of the type comprising a coil-form drive shaft and an acoustic transducer carried on the distal end of the drive shaft, is provided wherein a) the drive shaft includes at least a pair of inner and outer, concentric, oppositely and closely wound, hollow, multifilar coils; b) each coil has a ratio of outer radius of coil to thickness of coil filament in the radial direction of between about 2½ and 10; c) the coils are joined together at their respective ends with interfering contact with each other along their mutual length; and d) the filaments of each coil have a pitch angle of about 20° or greater, so that when drive torque is applied to the drive shaft from the proximal end in the direction tending to reduce the diameter and lengthen the outer coil and increase the diameter and shorten the inner coil, a substantial component of the resultant stress on each filament of the coils is aligned with the axis of the filament, whereby substantial mechanical fidelity of angular displacement between the transducer and the proximal end of the drive shaft is maintained during rotation of the drive shaft.

According to another aspect of the invention an acoustic catheter is provided comprising an elongated, flexible, liquid-confining catheter sheath and an elongated, flexible ultrasonic probe disposed within and rotatably supported by a lumen of the sheath, the ultrasonic probe comprising a transducer supported on the end of an elongated coil-form drive shaft, the exterior of the drive shaft being supported by the internal surface of the catheter lumen,' the inner diameter of the lumen being no more than about ¼ mm greater than the outer diameter of the drive shaft along most of their mutual length and being no more than about 1/10 mm greater than the outer diameter of the drive shaft in the distal region of the drive shaft and the transducer, a distal portion of the catheter sheath that corresponds with the position of the transducer being substantially transparent to acoustical energy-transmitted and received by the transducer and the probe and the sheath being cooperatively constructed and arranged to enable removal and replacement of the sheath in a disposable manner.

According to another aspect of the invention, there is provided a catheter sheath, per se, adapted to receive and rotatably support a predetermined elongated ultrasonic probe of the type comprising a coil-form rotatable drive shaft of predetermined length and an acoustic transducer carried on the distal end of the drive shaft, the path of rotation of the transducer having a diameter no greater than the drive shaft, the catheter sheath comprising a closed-end, elongated, flexible liquid-confining, resinous, flexible member having a lumen for receiving the probe, a distal portion of the sheath corresponding to the position of the rotatable transducer when inserted in the lumen being substantially transparent to acoustical energy transmitted and received by the transducer, the internal surface of the lumen sized to rotatably support the drive shaft.

The invention also features oppositely wound coils of a flexible acoustic probe drive shaft in torsionally prestressed condition in the direction causing the outer coil to bear radially in tight contact upon the inner coil. The invention also features means at the distal end of an acoustic probe drive shaft adapted to apply dynamic drag to the rotation of the flexible shaft to enhance the mechanical fidelity of angular displacement between the proximal and distal ends of the probe.

Preferred embodiments of the invention feature the drive shaft having an outer diameter throughout its length of about 1 mm or less; a liquid-filled, relatively fixed, first sheath portion closely surrounding a segment of the distal end of the drive shaft, adapted to apply dynamic, viscous drag to the shaft during its rotation, to enhance the mechanical fidelity of angular displacement between the proximal and distal ends of the probe; the difference between the outer diameter of the shaft segment and the inner diameter of the corresponding sheath portion being in the range of about 0.05 to 0.15 mm; a second sheath portion extends a substantial distance proximally from the first sheath portion, the second sheath portion being radially spaced a greater distance from the drive shaft than the radial spacing of the first sheath portion from the shaft segment; a continuous flexible resinous sheath, of which the first sheath portion is part, encloses the transducer and drive shaft, the portion of the sheath that corresponds with the position of the transducer being substantially transparent to acoustical energy transmitted and received by the transducer; the sheath includes a catheter sheath having an outer diameter throughout its length of less than about 3 mm; the outer surface of the outer coil of the drive shaft has a liquid-pumping screw-form contour, whereby, when the drive shaft, while exposed to liquid in the sheath, is driven in the direction tending to decrease the diameter of the outer coil, the outer surface of the coil is effective to pressurize liquid distally thereof; there is fluid communication between the liquid-filled space along the drive shaft and the space occupied by the transducer, whereby the action of the screw-form contour of the shaft is effective to pressurize liquid in which the transducer is immersed; the sheath includes a catheter sheath having a distal projection supported by the catheter sheath and extending distally from the position of the transducer; the distal projection includes a catheter extension having a diameter of the order of the diameter of the catheter sheath in the region of the transducer, the projection adapted to maintain alignment of the probe with a passage of interest as the probe is moved axially for varying the view of features in the region of the passage; the distal projection includes an elongated guide means of smaller diameter and greater flexibility than the catheter sheath; the distal projection includes means to introduce contrast medium or other fluid distal of the probe; the elongated ultrasonic probe disposed within a lumen of a catheter sheath, the internal bore of the lumen serving to rotatably support the probe, a distal portion of the catheter sheath that corresponds with the position of the transducer being substantially transparent to acoustical energy transmitted and received by the transducer; and the probe and the sheath are cooperatively constructed and arranged to enable removal and replacement of the sheath in a disposable manner.

In preferred embodiments, the transducer includes a single transducer element directed at an angle to the axis of the drive shaft, and there are provided means for rotating the shaft at a speed of the order of 1800 rpm, a means for energizing the transducer to cause it to emit at a frequency in excess of about 15 MHz, position detecting means at the proximal end of the drive shaft for detecting the instantaneous angular position of the shaft to represent the instantaneous angular position of the transducer, and TV monitor means responsive to return signals from the transducer and the position detecting means for providing a display of an acoustical image based upon signals detected by the transducer.

In preferred embodiments, the portion of the catheter sheath which is substantially transparent to acoustical energy is integral (i.e., without a joint) with a proximal portion of the catheter sheath; the substantially transparent portion of the catheter sheath has a thinner wall than the proximal portion; and the catheter sheath includes a resinous substance.

Another preferred embodiment includes the elongated probe or catheter described above, in combination with a hollow trocar adapted to receive the probe or catheter, the trocar having a side-facing window adapted to register with the transducer enabling the transducer to form acoustic images of tissue into which the trocar has been forced.

Other aspects, features and advantages of the invention will be apparent from the following description of the preferred embodiments and from the claims.

The invention enables the achievement of micro-acoustic, close-up imaging, via catheter, of restricted regions of the body that are difficult of access.

One object of the invention is to improve dilatation procedures such as angioplasty by ultrasonic viewing of a body lumen to locate the region to be treated and properly position the balloon, then continuously observe the occluded region as the angioplasty procedure progresses. Finally, after treatment, the treated region of the body lumen could be inspected to determine the efficacy of the procedure. It is therefore one object of this invention to provide a dilatation catheter having an ultrasonic probe.

BRIEF DESCRIPTION OF THE DRAWINGS

FIG. 4 is a longitudinal, cross-sectional view of the distal end of the assembled acoustic catheter;

FIG. 5 is a longitudinal sectional view of the transducer element of the catheter on a greatly magnified scale;

FIG. 6 is a diagrammatic representation of sound waves emanating from the acoustic lens of the catheter;

FIGS. 7 through 7d illustrate steps in filling the sheath and assembling the acoustic catheter of the figures, the syringe portions of the figures being on a reduced scale;

FIG. 8 is a cross-sectional view of the motor-connector assembly to which the catheter is connected while

FIG. 16 illustrates a combination balloon dilatation/acoustic imaging catheter sheath while

FIG. 17 is a view of a preferred embodiment of an acoustic imaging balloon angioplasty catheter;

FIG. 17a is an expanded view of the distal end of the balloon catheter;

FIGS. 17b and 17c are partial cross-sectional views 25 taken along the lines AA in FIG. 17a;

FIG. 17c is an expanded view of FIG. 17b;

FIG. 17d is an expanded view of the proximal end of the catheter coupling, in partial cross-section;

FIG. 19 is a view of an alternative embodiment of an acoustic imaging dilatation balloon catheter;

FIGS. 20–20b are views of alternative embodiments of an acoustic imaging dilatation balloon catheters enabling relative axial positioning of the transducer and the balloon;

FIGS. 21–21b are views of alternative embodiments of an acoustic imaging balloon catheters, including multiple balloons;

FIGS. 22 and 22a illustrate an acoustic catheter sheath adapted for guidance by a guide wire;

FIG. 23 illustrates an acoustic catheter sheath which is deflectable by actuation from the proximal end;

FIGS. 24 and 24a illustrate an acoustic catheter sheath capable of injection of a fluid;

FIGS. 25 through 25c illustrate the combination of an acoustic catheter with a trocar;

FIG. 26 illustrates an integrally formed acoustic catheter sheath;

FIG. 27 illustrates an acoustic catheter sheath having an integral flexible distal extension;

DETAILED DESCRIPTION OF THE PREFERRED EMBODIMENTS

General Structure

Figure 1:
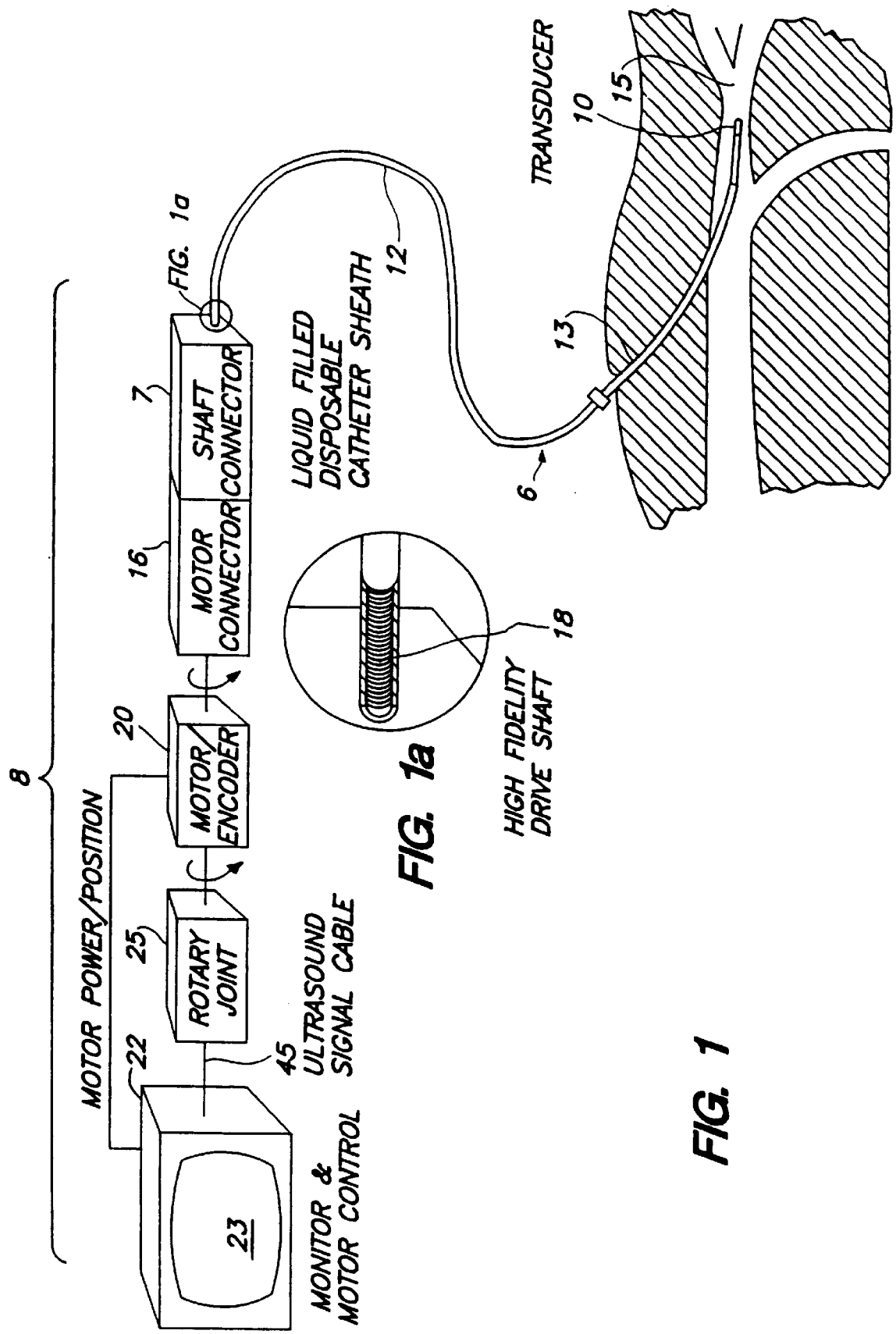
FIG. 1 is a schematic diagram of a preferred system showing use of an acoustic catheter according to the invention.

Referring to FIG. 1, a micro-acoustic imaging catheter 6 according to the invention is driven and monitored by a control system 8. The catheter is comprised of a disposable catheter sheath 12 (FIGS. 2 and 4) having a sound-transparent distal window 24 provided by dome element 25 (FIG. 4), in which is disposed a miniature, rotatable ultrasonic transducer 10 (FIGS. 3 and 4) driven by a special, high fidelity flexible drive shaft 18. A relatively rigid connector 11 is joined to the proximal end of the main body of the sheath, adapted to be joined to a mating connector of drive and control system 8.

The catheter is adapted to be positioned in the body by standard catheter procedures; for example, within a blood vessel or the heart by guiding the flexible catheter through various blood vessels along a circuitous path, starting, for example, by percutaneous introduction through an introducer sheath 13 disposed in a perforation of the femoral artery 15.

Figure 2:
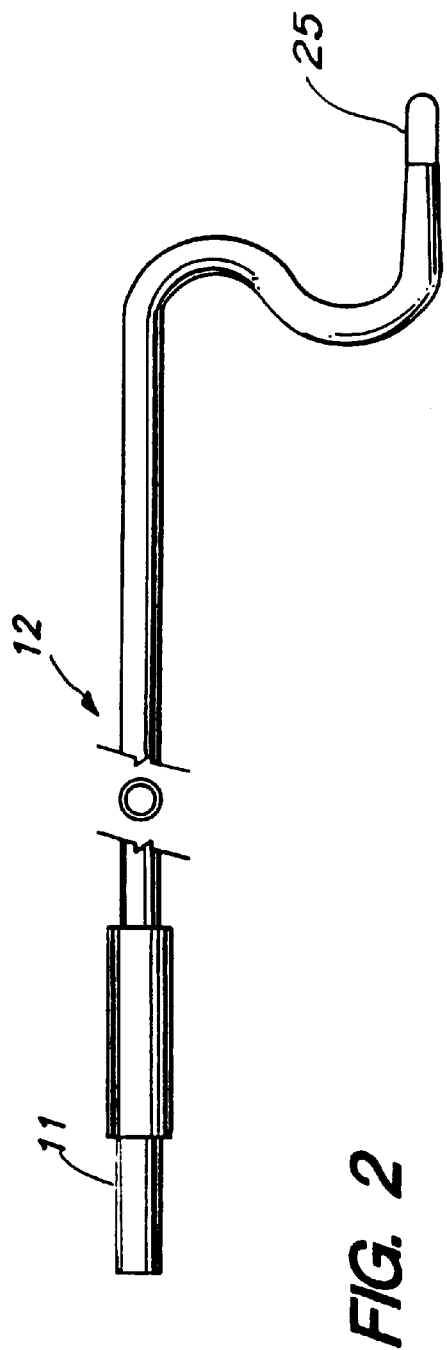
FIG. 2 is a side view of a disposable catheter sheath for the acoustic catheter.

Referring to FIG. 2, disposable catheter sheath 12 is a long tube, extruded from standard catheter materials, here nylon, e.g., with outer diameter, D, of 2 mm, wall thickness of 0.25 mm and length of 1 meter. Dome element 25, connected to the distal end of the tube, is a semi-spherically-ended cylindrical transducer cover constructed of material which is transparent to sound waves, here high impact polystyrene. This dome element has a thickness of approximately 0.125 mm and a length E of about 8 mm. For purposes described later herein, catheter sheath 12 in its distal region preferably tapers down over region R as shown in FIG. 4 to a narrowed diameter D' at its distal end, achieved by controlled heating and drawing of this portion of the original tube from which the sheath is formed. Catheter sheath 12 and acoustically transparent 30 dome element 25 are adhesively bonded together.

Figure 3:
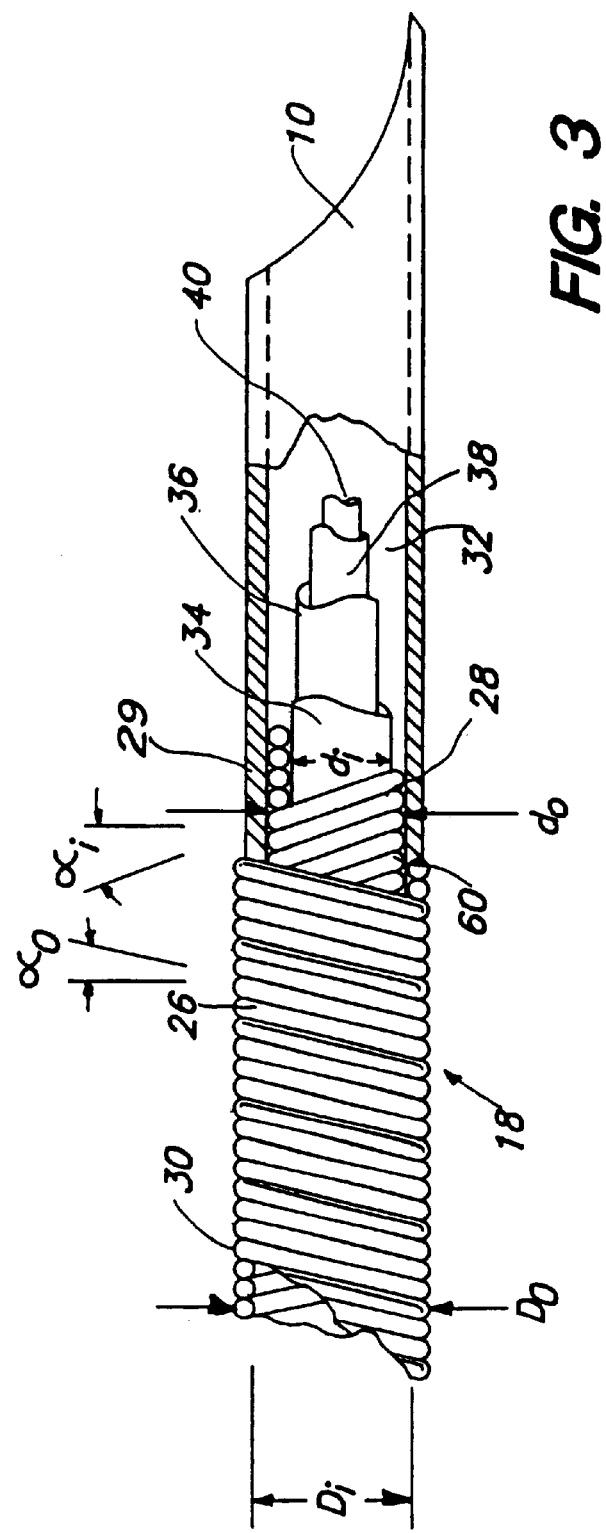
FIG. 3 is a longitudinal, partially cut away view of the distal end of the rotating assembly of the acoustic catheter.

Referring to FIGS. 3 and 4, the drive shaft assembly 18 is formed of a pair of closely wound multi-filar coils 26, 28 wound in opposite helical directions. These coils are each formed of four circular cross-sectional wires, one of which, 30, is shown by shading. Coils 26, 28 are soldered together at both the distal and proximal ends of the assembly in interference contact, here under rotational pre-stress. By also providing a pitch angle of greater than about 20°, a substantial part of the stress applied to the wire filaments of the coil is compression or tension in the direction of the axis of the filaments, with attendant reduction of bending tendencies that can affect fidelity of movement. There is also provision to apply a torsional load to the distal end of the assembly to cause the drive shaft to operate in the torsionally stiff region of its torsional spring constant curve, achieved by viscous drag applied to the rotating assembly by liquid filling the narrowed distal end of the catheter sheath (FIG. 4). Such loading, together with initial tight association of the closely wound filaments in the concentric coils, provides the assembly with a particularly high torsional spring constant when twisted in a predetermined direction. Thus, despite its lateral flexibility, needed for negotiating tortuous passages, the assembly provides such a torsionally stiff and accurate drive shaft that rotary position information for the distal end can, with considerable accuracy, be derived from measurement at the proximal end of the drive shaft, enabling high quality real-time images to be produced. (Further description of the coils of the drive shaft and their condition of operation is provided below.)

Coaxial cable 32 within coils 26, 28 has low power loss and comprises an outer insulator layer 34, a braided shield 36, a second insulator layer 38, and a center conductor 40. Shield 36 and center conductor 40 are electrically connected by wires 42, 44 (FIG. 5) to piezoelectric crystal 46 and electrically conductive, acoustical backing 48 respectively, of the transducer. Helical coils 26, 28, especially when covered with a highly conductive metal layer, act as an additional electric shield around cable 32.

Transducer crystal 46 is formed in known manner of one of a family of ceramic materials, such as barium titanates, lead zirconate titanates, lead metaniobates, and PVDFs, that is capable of transforming pressure distortions on its surface to electrical voltages and vice versa. Transducer assembly 10 is further provided with an acoustic lens 52. The radius of curvature B of lens surface 52 is greater than about 2.5 mm, chosen to provide focus over the range f (FIG. 6) between about 2 to 7 mm. The lens is positioned at an acute angle to the longitudinal axis of the catheter so that, during rotation, it scans a conical surface from the transducing tip, the angle preferably being between 10° and 80°, e.g., 30°. Transducer backing 48 is acoustically matched to the transducer element to improve axial resolution.

The transducer assembly 10 is supported at the distal end of the drive shaft by a tubular sleeve 29 which is telescopically received over a distal extension of the inner coil 28, as shown in FIG. 3.

Referring again to FIG. 4, the length, E, of dome 25 element 25 is sufficient to provide headroom F for longitudinal movement of transducer 10 within the dome element as catheter sheath 12 and coils 26, 28 are twisted along the blood vessels of the body. In the untwisted state, transducer 10 is a distance F, about 2 to 3 mm, from the internal end surface of the dome element 25. The dome element, along with catheter sheath 12 is adapted to be filled with lubricating and sound-transmitting fluid.

Figure 7:
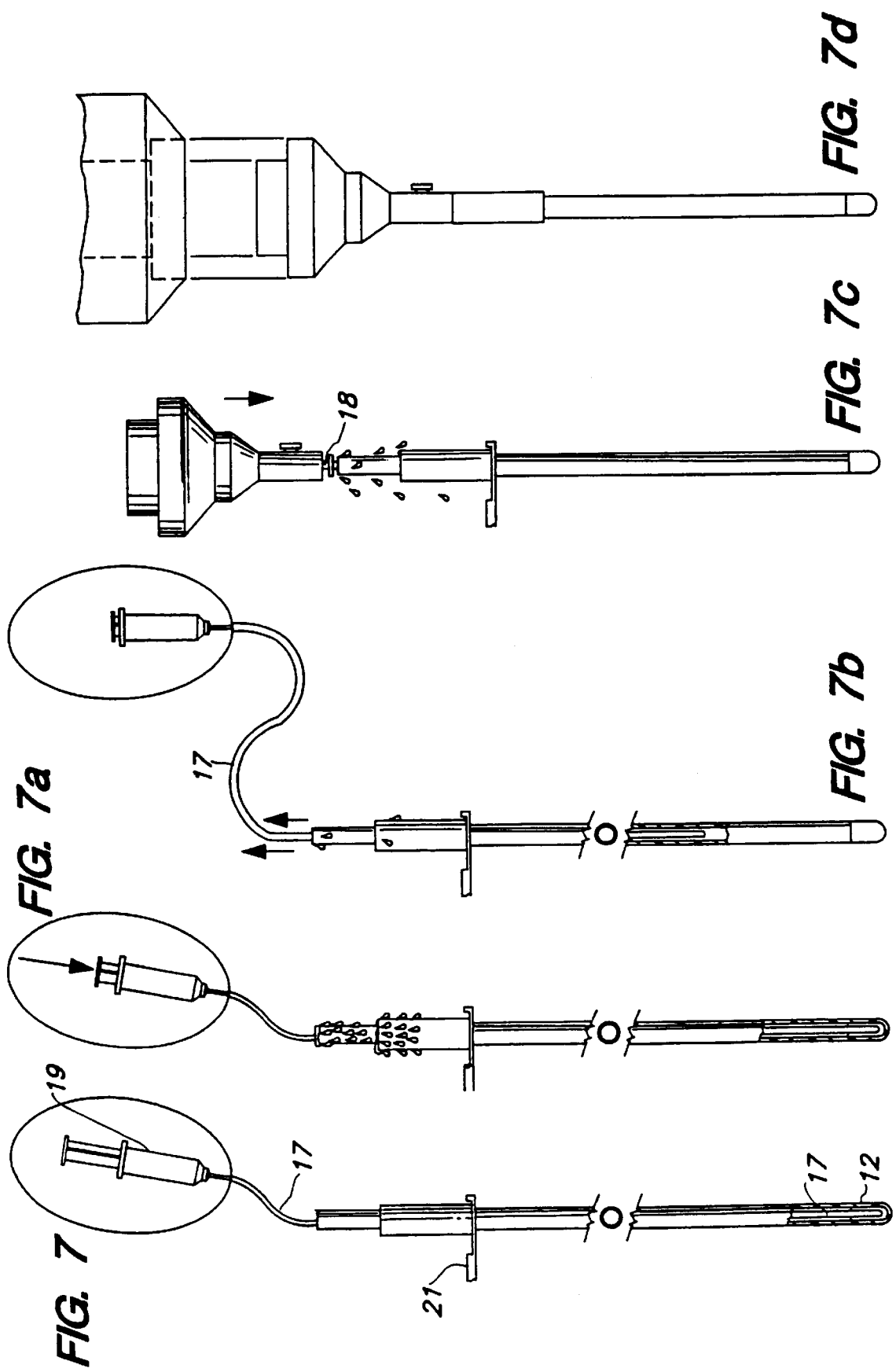

FIGS. 7–7b show the filling procedure used to prepare ultrasound catheter sheath 12 (or any of the other interchangeable sheaths, see FIGS. 13–26) for attachment to the ultrasound imaging driveshaft and transducer assembly. A sterile, flexible filling tube 17 attached to a syringe 19 is filled with sterile water. This filling catheter is inserted into the ultrasound catheter sheath 12, all the way to the distal tip. The water is then injected until it completely fills and the excess spills out of the ultrasound catheter while held in a vertical position (see FIG. 7a). This expels air from the catheter which could impair good acoustic imaging. Continued pressure on the plunger of the syringe causes the flexible tube 17 to be pushed upward, out of catheter 12, FIG. 7b, leaving no air gaps behind. This eliminates the necessity to carefully withdraw the flexible filling tube at a controlled rate which could be subject to error. A holding bracket 21 is used to hold the catheter vertical during this procedure.

After the catheter sheath 12 is filled, the acoustic 20 transducer 10 and shaft 18 are inserted, displacing water from the sheath 12, until the installed position, FIG. 7d, is achieved.

Figure 8:
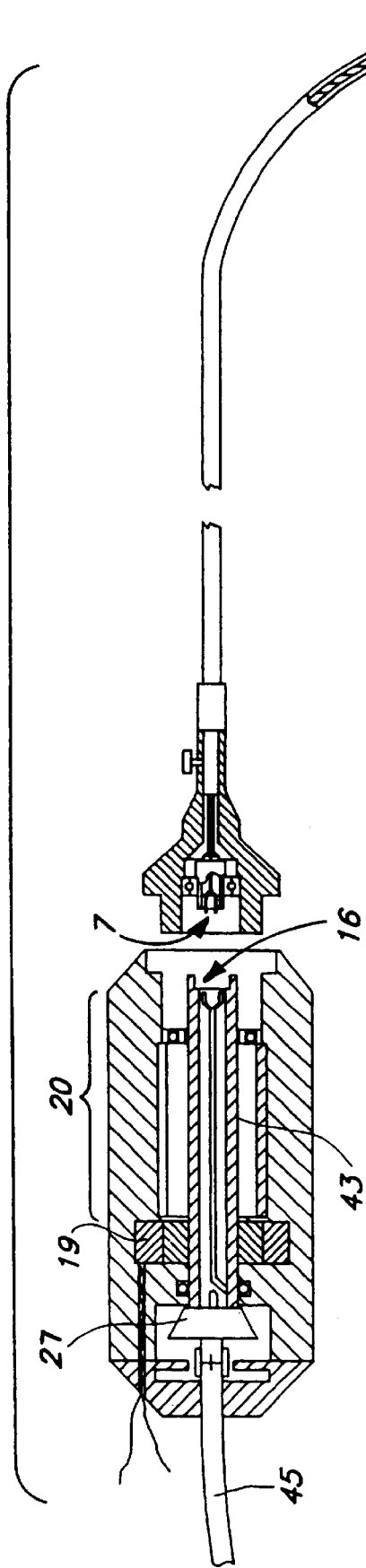
Figure 8A:
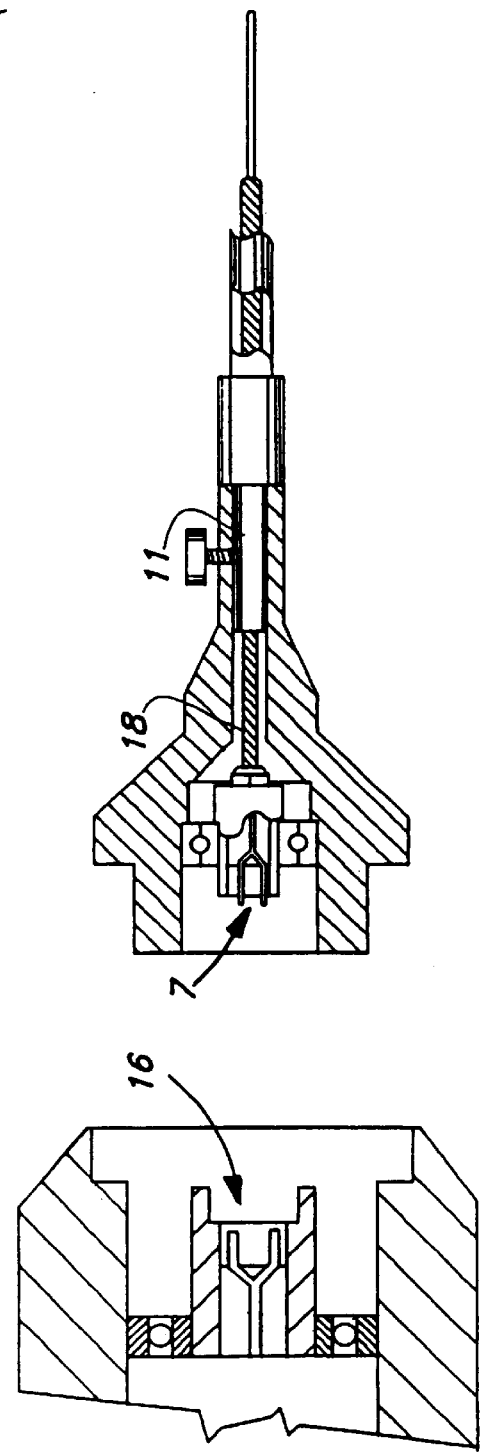
FIG. 8a is a view on an enlarged scale of a portion of FIG. 8.

FIGS. 8 and 8a (and FIG. 1, diagrammatically) show the interconnection arrangement for a connector 7 at proximal end of the acoustic catheter with connector 16 of the driving motor 20, and the path of the electric wires through the center shaft 43 of the driving motor. The center shaft and connector 16 rotate together, as do the wires that pass through the hollow motor shaft. The latter connect to a rotating electrical joint 27, which is held stationary at the back end and is connected to stationary coaxial cable 45 through a suitable connector such as a common BNC type. The enlarged view shows how the motor connector 16 and the driveshaft connector 7 mate when the two assemblies are pushed together, thereby making both electrical and mechanical contact. The catheter connector 7 is held in position by an ordinary ball bearing which provides a thrusting surface for the rotating connector 16 and driveshaft 18 while allowing free rotation. The disposable catheter sheath 12 includes an inexpensive, relatively rigid hollow bushing 11 of cylindrical construction that allows it to be slid into and held by means of a set screw in the housing that captures the non-disposable bearing, connector, and driveshaft 18. Driveshaft coil assembly 18, thus attached at its proximal end to connector 16 of drive motor 20, rotates transducer 10 at speeds of about 1800 rpm. The transducer 10 is electrically connected by coaxial cable 32 extending through coil assembly 18 and via the cable through the motor to the proximal electronic components 22 which send, receive, and interpret signals from the transducer. Components 22 include a cathode ray tube 23, electronic controls for the rotary repetition rate, and standard ultrasonic imaging equipment (see FIG. 12). A rotation detector, in the form of a shaft encoder shown diagrammatically at 19, detects the instantaneous rotational position of this proximal rotating assembly and applies that positional information to components 22, e.g., for use in producing the scan image.

By thus depending upon the position of proximal components to represent the instantaneous rotational position of the distal components, the rotational fidelity of the drive shaft is of great importance to this embodiment.

Manufacture and Assembly of the Drive Shaft

Referring to FIGS. 3 and 4, coils 26, 28 are each manufactured by winding four round cross-section stainless steel wires of size about 0.2 mm, so that $D_o$ is about 1.3 mm, $D_i$ is about 0.9 mm, $d_o$ is about 0.9 mm and $d_i$ is about 05 mm. The coils are closely wound with a pitch angle $\alpha_o$ and $\alpha_i$ where $\alpha_o$ is smaller than $\alpha_i$, e.g., 22½° and 31°, respectively. (Flat wires having a cross-sectional depth of about 0.1 mm may also be used.) The pitch angles are chosen to eliminate clearances 60 between the wires and to apply a substantial part of the stress in either tension or compression along the axis of the wire filaments. The coils, connected at their ends, are adapted to be turned in the direction tending to make outer coil 26 smaller in diameter, and inner coil 28 larger. Thus the two assemblies interfere with each other and the torsional stiffness constant in this rotational direction is significantly increased (by a factor of about 6) due to the interference. Operation of the driveshaft in the torsionally stiff region with enhanced fidelity is found to be obtainable by adding a torsional load to the distal end of the rotating assembly of the catheter. The importance of rotational fidelity and 20 details how it is achieved warrant further discussion.

For ultrasound imaging systems, the relative position of the ultrasound transducer must be accurately known at all times so that the return signal can be plotted properly on the display. Any inaccuracy in position information will contribute to image distortion and reduced image quality. Because, in the preferred embodiment, position information is not measured at the distal tip of the catheter, but rather from the drive shaft at the proximal end, only with a torsionally stiff and true driveshaft can accurate position information and display be obtained.

Furthermore, it is recognized that any drive shaft within a catheter sheath will have a particular angular position which is naturally preferred as a result of small asymmetries. Due to this favored position, the shaft tends, during a revolution, to store and then release rotational energy, causing non-uniform rotational velocity. This phenomenon is referred to as "mechanical noise" and its effect is referred to as "resultant angular infidelity" for the balance of this explanation.

According to the present invention, use is made of the fact that suitably designed concentric coils interfere with each other, as has been mentioned previously. When twisted in one direction, the outer layer will tend to expand and the inner layer contract thus resulting in a torsional spring constant which is equal only to the sum of the spring constants of each of the two shafts. When, however, twisted in the opposite direction, the outer layer will tend to contract while the inner layer will expand. When interference occurs between the inner and outer layers the assembly will no longer allow the outer coil to contract or the inner to expand. At this point, the torsional spring constant is enhanced by the interference between the shafts and the torsional spring constant is found to become five or ten times greater than the spring constant in the "non-interference" mode.

Figure 9:
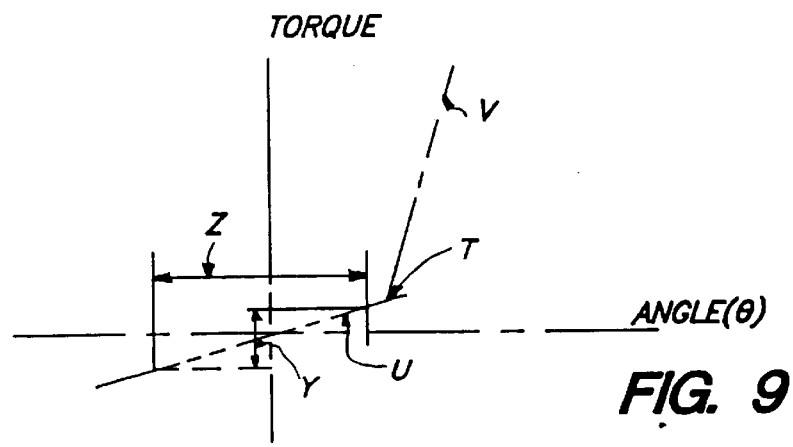
FIGS. 9, 10 and 11 are graphical representations of torque in relation to angular deflection.

Referring to FIG. 9, the relationship between torque 25 and angular deflection for such a coil assembly is shown, assuming one end fixed and torque applied at the opposite end. 'Y' represents mechanical noise; 'Z' resultant angular infidelity; 'T' the interference point; the slope of the line 'U', the torsional spring constant (TSC) without interference (i.e., the sum of the torsional spring constant of each of the two coils); and the slope of the line 'V', the TSC with interference. Thus, TSC is shown to increase dramatically at the interference point.

Figure 10:
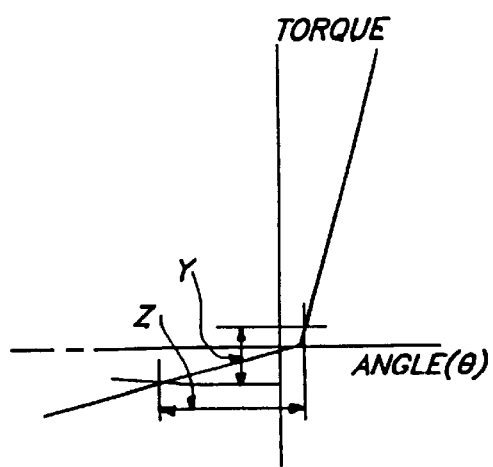

Referring to FIG. 10, by pre-twisting the shafts relative to one another and locking their ends together in a pre-loaded assembly, the interference point is moved to be close to the rest angle and resultant angular infidelity, Z, is reduced in the given direction of rotation.

Figure 11:
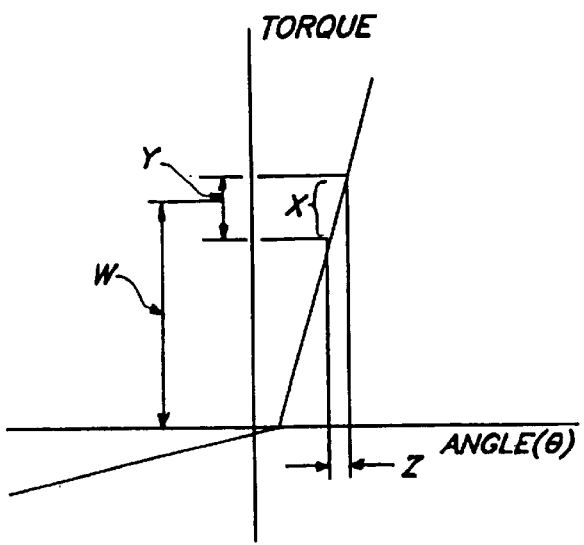

To improve upon this effect even further, dynamic frictional drag is intentionally introduced at the distal end of the shaft to raise the level of torque being continually applied to the system. This ensures operation of the shaft in the region of the high torsional spring constant or "interference" mode throughout its length, producing a rotationally stiffer shaft. This is shown in FIG. 11, where 'W' is dynamic load and 'X' is the region of operation. The use of such dynamic drag is of particular importance in certain catheters of small diameter, e.g., with outer diameter less than about 2 mm.

To form inner coil 28, four individual wires are simultaneously wound around a mandrel of about 0.5 mm outer diameter. The free ends of this coil are fixed, and then four wires are wound in opposite hand directly over this coil to form the outer coil 26. The wires are wound under moderate tension, of about 22.5 gm/wire. After winding, the coils are released. The inner mandrel, which may be tapered or stepped, or have a constant cross-sectional diameter, is then removed. The wire ends are finished by grinding. One end is then soldered or epoxied to fix the coils together for a distance of less than 3 mm. This end is held in a rigid support and the coils are then twisted sufficiently, e.g., ¼ turn, to cause the outer coil to compress and the inner coil to expand, causing the coils to interfere. The free ends are then also fixed.

The coil assembly 18 is generally formed from wires which provide a low spring index, that is, the radius of the outer coil 26 must be not more than about 2.5 to 10 times the diameter of the wires used in its construction. With a higher index, the inner coil may collapse. The multi-filar nature of the coils enables a smaller diameter coil to be employed, which is of particular importance for vascular catheters and other catheters where small size is important.

After the coil assembly is completed, coaxial cable 32 is inserted within the inner coil. The cable may be silver-coated on braid 36 to enhance electrical transmission properties. It is also possible to use the inner and outer coils 26, 28 as one of the electrical conductors of this cable, e.g. by silver coating the coils.

Referring back to FIGS. 3 and 5, to form transducer 10, wire 42 is soldered to either side of electrically conducting sleeve 29 formed of stainless steel. Wire 44 is inserted into a sound absorbent backing 48 which is insulated from sleeve 29 by insulator 72. Piezoelectric element 46 of thickness about 0.1 mm is fixed to backing 48 by adhesive and electrical connection 74 is provided between its surface and the end of sleeve 29. Thus, wire 42 is electrically connected to the outer face of piezoelectric element 46, and wire 44 electrically connected to its inner face. Spherical lens 52, formed of acoustic lens materials is fixed to the outer surface of element 46.

Referring to FIGS. 4 and 7–7d, the completed drive shaft 18 and transducer 10 are inserted into disposable catheter sheath 12, positioning transducer 10 within acoustically transparent dome element 25, with liquid filling the internal open spaces. The catheter thus prepared is ready to be driven by the drive assembly; see FIG. 8.

During use, rotation of drive shaft 18, due to exposure of the helical surface of the outer coil to the liquid, tends to create helical movement of the liquid toward the distal end of the sheath. This tends to create positive pressure in dome element 25 which reduces the tendency to form bubbles caused by outgassing from the various surfaces in this region.

As has been mentioned, it is beneficial to provide added drag friction at the distal end of the rotating drive shaft 18 to ensure operation in the torsionally stiff region of the torsional spring constant curve. it is found that this may be done by simply necking down the distal portion of the catheter sheath 12, as shown in FIG. 4 to provide a relatively tight clearance between the distal portion of the shaft 18 and the inner surface of the sheath, to impose the desired degree of viscous drag. As an alternative, the dynamic drag may be provided by an internal protrusion in catheter sheath 12 to create a slight internal friction against drive shaft 18.

A preferred acoustic catheter is constructed so that it may be preformed prior to use by standard methods. Thus, if the investigator wishes to pass the catheter through a known tortuous path, e.g., around the aortic arch, the catheter can be appropriately shaped prior to insertion. Such preformation can include bends of about 1 cm radius and still permit satisfactory operation of the drive shaft.

Electronics

Figure 12:
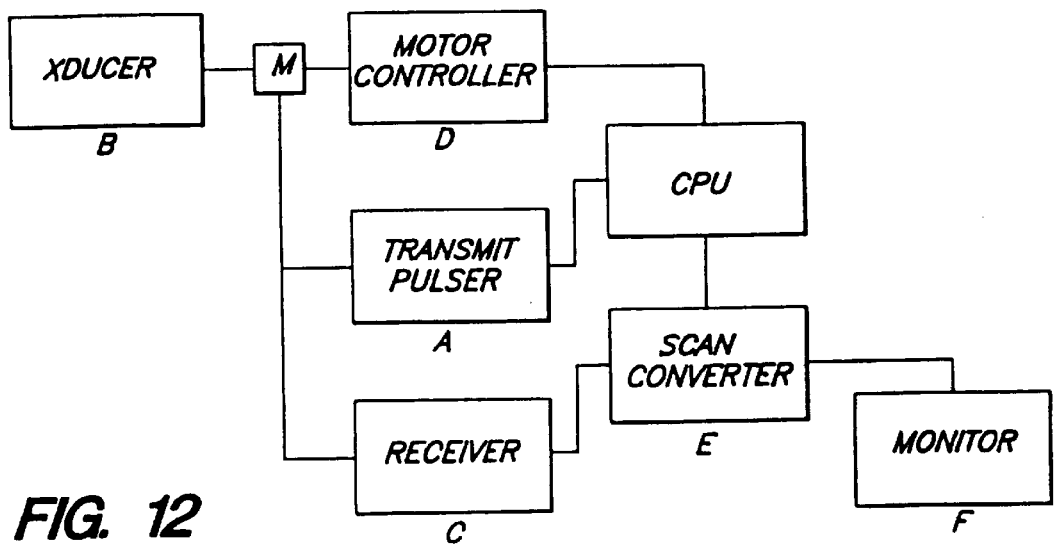
FIG. 12 is a block diagram of the electronic components useful with the acoustical catheter of the invention.

FIG. 12 is a block diagram of the electronics of a basic analog ultrasound imaging system used with the acoustical catheter. The motor controller (D) Positions the transducer B for the next scan line. The transmit pulser (A) drives the ultrasound transducer. The transducer (B) converts the electrical energy into acoustic energy and emits a sound wave. The sound wave reflects off various interfaces in the region of interest and a portion returns to the transducer. The transducer converts the acoustic energy back into electrical energy. The receiver (C) takes this waveform and gates out the transmit pulse. The remaining information is processed so that signal amplitude is converted to intensity and time from the transmit pulse is translated to distance. This brightness and distance information is fed into a vector generator/scan converter (E) which along with the position information from the motor controller converts the polar coordinates to rectangular coordinates for a standard raster monitor (F). This process is repeated many thousands of times per second.

By rotating the transducer at 1800 rpm, repeated sonic sweeps of the area around the transducer are made at repetition rate suitable for TV display, with plotting based upon the rotary positional information derived from the proximal end of the device. In this way a real time ultrasound image of a vessel or other structure can be observed.

We have found that within a blood vessel imaging 20 system a focal point of between 1 and 7 mm is suitable and that a frequency of 15 to 40 MHz provides good resolution of vessel features in a practical manner.

Use

As mentioned above, the acoustical imaging catheter 25 may be introduced by standard techniques, Preferably by percutaneous insertion, into any desired blood vessel. Alternatively, it can be introduced directly into a body cavity or body tissue such as an organ. Due to its rotational fidelity, the device provides a relatively high quality, real time image of blood vessel tissue and allows ready diagnosis of disease states such as occlusion or dyskinesia. The acoustic properties of various tissues can also be discerned to allow more accurate diagnosis. It is also possible to form three-dimensional images using appropriate computer software and by moving the catheter within the blood vessel. The device is also useful in angioplasty therapy to determine the nature and geometry of intravascular protrusions. This device may be combined with existing optical devices to provide a device having an ultrasonic visualizing probe and a laser ablating ability. The device may also be used in diagnosis of, e.g., esophageal tumors or prostate carcinomas, by passing the catheter through the anus, urethra, trachea, or esophagus. The catheter is also useful for valvuloplasty by insertion through a cardiac valve. Further, in non-medical areas, the device is useful for any inaccessible passages which are fluid filled, and thus transmit sound waves.

Selectable Catheter Sheaths

A wide variety of novel disposable catheter sheaths can be substituted for catheter sheath 12 and used in the system.

Figure 13A:
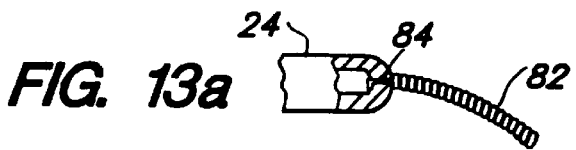
FIGS. 13 and 13a illustrate an acoustic imaging catheter sheath having a distal floppy guide wire.
Figure 13:
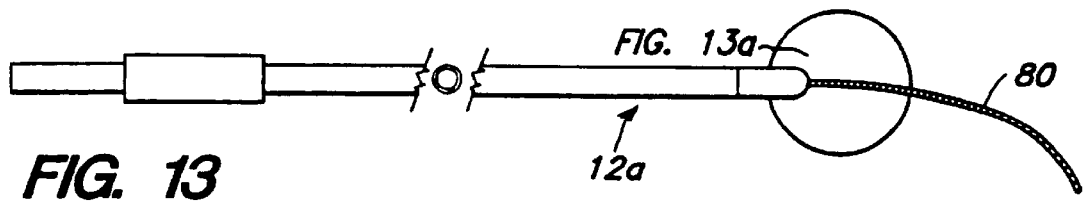

FIGS. 13 and 13a show a flexible, disposable catheter sheath 12a that is constructed like sheath 12 and has, in addition at its distal tip, a floppy guide wire 80 which is useful for guiding the ultrasound device through a valve such as of the heart. The guide wire is constructed of a closely wound wire coil 82 and an internal safety wire 84 for added strength. Wire 84 is welded to the distal tip of coil wire 82 and its proximal end is bent over within dome 25 and securely anchored with epoxy cement. In another embodiment, the safety wire extends through a separate lumen of the catheter sheath to a securing point at the proximal end of the catheter. In addition to its guiding function, coil 80, with suitable variation of length and stiffness, is useful in supporting and steadying the free end of the ultrasound device during axial movement of the catheter to improve its imaging capability; see, e.g., FIGS. 30–30c.

Figure 14A:
FIGS. 14 and 14a illustrate an acoustic imaging catheter sheath having a distal anchoring needle.
Figure 14:
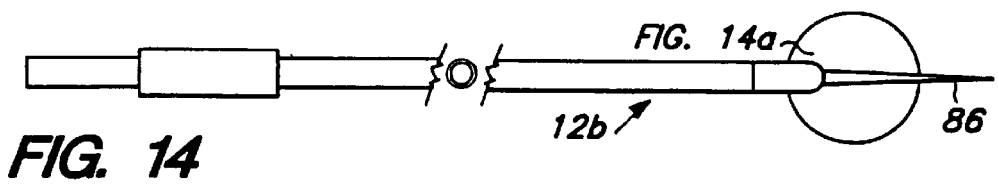

FIG. 14 shows sheath 12b having needle 86 securely anchored to the tip, useful for impaling a surface, such as that found in the interior of the heart, and temporarily anchoring and steadying the ultrasound device in a fixed position. In another embodiment, it too can have a safety wire extending to a proximal securing point. This acoustic catheter may be introduced through an introducing catheter. In another embodiment, the needle can be retracted during introduction.

Figure 15:
FIG. 15 illustrates an acoustic imaging catheter 15 sheath having a distal catheter extension beyond the transducer.

FIG. 15 shows another flexible, disposable sheath 12c that is constructed so that the sonolucent (acoustically transparent) portion 24a is spaced from the distal end instead of at the end. The extension 12x beyond the window 24a may be of the same flexible catheter material as the main body of the sheath or of a different, e.g. softer material, and may be either open, so that fluids may pass through it, or closed, so that no fluids pass through. The distal extension of the catheter sheath can serve to stabilize the lateral position of the transducer during axial movement of the catheter during imaging.

Figure 16:
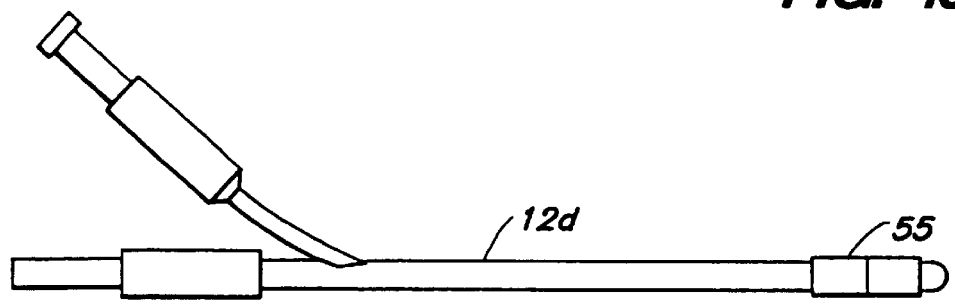
Figure 16A:
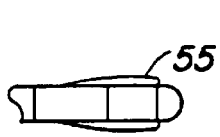
FIGS. 16a, 16b and 16c illustrate stages of inflation of the balloon.
Figure 16B:
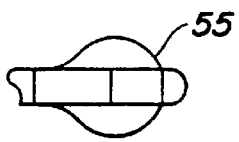
Figure 16C:
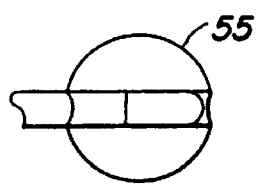

FIG. 16 shows a catheter sheath 12d on which is mounted, over the transducer area, a dilatation balloon 55 such as is commonly used for angioplasty. The balloon is adapted to be pressurized with liquid, such as water, through the same lumen that holds the ultrasound imaging device, via an inflation opening in the wall of the catheter sheath. This catheter is used to open a clogged, stenotic or narrowed passage in the body, while simultaneously measuring the progress of the dilatation procedure with the ultrasound images. Another embodiment with a suitable balloon may be used to center or position the ultrasound device securely within a body passage or cavity and maintain its position away from a feature of interest, for instance for imaging a wall of the heart. The balloon in its collapsed or unpressurized state is easily inserted prior to positioning and may be accurately positioned by use of ultrasound imaging during initial placement. In other embodiments a separate lumen is provided for inflation of the balloon and/or the balloon is spaced from the distal end of the catheter 10.

Referring to FIG. 17, a plan view of a preferred embodiment of an acoustic imaging balloon dilatation catheter system is shown. The system 120 includes a boot member 122 including a ferrule member 124 at its proximal end, constructed to enable electrical and mechanical 15 connection, as discussed for example with respect to FIGS. 8–8a, to the acoustic imaging control system, as discussed for example with respect to FIG. 1, for transmitting rotary power and control signals to the acoustic imaging transducer held within the balloon catheter sheath 139 near balloon 140 and for receiving acoustical image signals from the transducer to enable monitoring and control of the dilatation process, as will be further described below. The proximal end of the apparatus further includes a seal 126 (FIG. 17d) which enables intimate but relatively frictionless contact with the portion of the rotating drive shaft, and will also be further discussed below.

The catheter apparatus may be sized for use in various body cavities and applications such as the coronary arteries, peripheral arteries such as the iliac and femoral artery, the extremities, the esophagus, prostate and for valvuloplasty. In a preferred embodiment, shown in FIGS. 17–17c which may be of use in the peripheral arteries, for example, or the case of a dialysis shunt, a 6 F sheath 128 extends a distance of $L_1$, about 30 cm from the end of the seal 126 to a "Y" double flare compression fitting 130. Fitting 130 includes a side arm 132 for introduction of inflation fluid such as water or saline by means of a screw syringe 134 for inflation of balloon 140 near the distal end of the catheter 139. The side arm 130 further includes inner passageways for control wires (not shown) within the balloon for controlling a heating means enabling heating of the inflation fluid for the purpose of heated balloon angioplasty. The heater control wires may be passed, for example, through conduit 136 to heater control module 138.

Extending distally from the compression fitting 130 is catheter body sheath 139 which has an outer diameter of 4F and extends a distance $L_2$ about 92.5 cm to the center of the balloon 140. The catheter may be adapted to track a guidewire 152 which passes through a sonolucent saddle member 159 beneath the balloon and out of a distal extension 157 of the catheter, distal to the balloon. Also distal to the balloon is self-sealing septum tip 142 enabling introduction of saline or another fluid for purging the balloon of air bubbles that might impair acoustic imaging. Such a self-sealing septum is described in U.S. Pat. No. 5,002,059. The length of the system 120, from the end of the ferrule to the center of the balloon is $L_3$, about 132.5 cm and the length from the seal 126 to the center of the balloon is $L_4$, about 127.7 cm. The catheter 139 extends distally from the center of the balloon a distance $L_5$, about 3 cm. The balloon length, $L_6$, is about 4 cm (inflated diameter about 7–8 mm). The extension 157 distal to the balloon is $L_7$, about 1.5 cm. The catheter length is about 95 cm.

Referring to FIG. 17a the distal end of the catheter is shown in partial cross-section with the balloon deflated and inflated (phantom). A rotating ultrasound transducer 146 having a coil form drive shaft 141, as discussed herein above, is positioned on the central axis A of the catheter sheath 139 at a position corresponding to the inflatable dilatation balloon 140. The catheter sheath 139 forms a sonolucent guide for the transducer 146 and drive shaft. The catheter sheath is formed of a thin (0.005 to 0.007 inch) sonolucent material such as polyethylene to provide sufficient guidance for the drive shaft and transducer without causing excessive attenuation of the ultrasound signal emitted by the transducer. The catheter body material, the balloon material, and the guidewire saddle are in general selected to be sonolucent and have an acoustic impedance substantially matched to the body fluid, e.g., blood, to which the catheter is exposed, to minimize attenuation of the acoustic signals emitted and received from the transducer. Polyethylene is advantageous in that it has an acoustic impedance that substantially matches blood and saline, it is capable of withstanding high dilatation pressures and is only slightly elastic, enabling a reliable balloon inflation diameter. An advantage of the present system, which allows observation of balloon inflation during dilatation, is that balloon materials with some elasticity may be employed without danger of over-inflation within a lumen since the operator can suspend inflation in response to the acoustic image at any time during treatment. It will be understood that the catheter may be formed having sonolucent regions corresponding to the location of the transducer while the rest of the catheter is not sonolucent, e.g., made of thicker material. Fluid communication between the balloon and the catheter is provided through port 151 to equalize the fluid pressure encountered during dilatation between the balloon and within the catheter to reduce the risk of collapse of the typically thin, sonolucent catheter and subsequent undesirable binding of the driving shaft which rotates the transducer, when the balloon is inflated at relatively high pressures, e.g., over 100 psi for balloon angioplasty procedures.

The dilatation balloon 140 which is preferably polyethylene, as discussed, may be mounted at its ends 147, 148 over the guidewire saddle by, for example, melt-sealing. The balloon may also be secured to the saddle by clips or the like as conventionally known. Prior to mounting the balloon in this area, the catheter is fitted with the sonolucent saddle 159 that extends under the area of the balloon and exits distally and proximally beyond the ends of the balloon. The saddle enables the use of a thin walled single lumen catheter body that is substantially sonolucent. Further, the use of single lumen catheters enables smaller catheter sizes to be employed, for example, 3F catheters which can be used in coronary arteries. The saddle guide, as shown in cross section in FIG. 17b (taken along line A—A of FIG. 17a) and in FIG. 17c, is a tubular member disposed over the catheter having a bowed or stretched Portion that creates a lumen in which the guidewire is placed. The saddle inner lumen is of sufficient clearance to allow the catheter to track over a guidewire. The saddle ends 154, 155 are angle cut and smooth edged to allow ease of entry of and guidance by the guide wire 152. The saddle is preferably formed of polyethylene having a wall thickness $T_1$, of about 0.004 inch. The thickness of the catheter body wall is $T_2$, is about 0.007 inch. The guidewire diameter is $D_1$ about 0.018 inch and the drive shaft is of a diameter $D_2$ of about 0.045 inch. Referring back to FIG. 17a the guide wire passes through a side aperture 153 in the extension 157 of the catheter 139 distal to the balloon, through the inner lumen of the extension 157 and a distal aperture 161. As indicated, the guidewire is exposed to the body lumen except for its passage through the saddle and distal extension of the catheter. The saddle may be, for example, disposed around the entire circumference of the catheter along a continuous length of the catheter corresponding to the length of the balloon in which case a port at a location corresponding to the port 151 must be provided in the saddle, or optionally, the saddle may be disposed around the entire circumference of the catheter only at its proximal and distal ends, and partially about the circumference therebetween, enabling free flow from port 151.

The distal tip of the catheter is fitted with self-sealing septum 158 to allow introduction of saline or the fluid distally, forcing air bubbles that might impair acoustic imaging and successful balloon inflation proximally. Alternately, the septum may be used as an air vent when a needle is inserted, allowing the catheter to be filled with fluid from a side arm, in which case bubbles and undesirable air may be expelled efficiently and completely. The septum is more completely described in U.S. Pat. No. 5,002,059.

For heating the balloon inflation fluid, annular electrical contacts 143, 144 inside of balloon 140 are bonded directly to the catheter sheath 139. The contacts are positioned on either side of the transducer 146 and are spaced apart approximately half the length of the balloon. The spacing from the respective ends of the balloon is approximately one fourth the length of the balloon, so that the balloon will heat evenly. The contacts 143 and 144 connect to opposite poles of current-controlled (constant current) radio frequency power supply in the control module 13. The catheter also includes a thermistor 145, located just proximally of the transducer 146 for measurements of balloon temperature.

Wires for the contacts and thermistor (not shown) are enclosed within catheter sheath 139 along its length, and exit catheter through a lumen, which is accessible from inside of balloon 140. The wires may also be provided in a separate lumen in a two-lumen guide catheter.

The control module includes an RF power supply that preferably operates at 650 kilohertz, but can be at any frequency within the range of about 100 kilohertz to 1 megahertz. The inflation fluid, while selected to have resistive losses, has an electrical impedance low enough that it will conduct the current supplied by RF power supply at voltages of about 100 volts or lower, so that there will be no arcing. A full description of a suitable RF heated balloon system is described in U.S. application Ser. No. 07/404,483, filed Sep. 8, 1989, and in U.S. Pat. No. 4,955,377. Furthermore, it will be understood that other methods for balloon heating may be employed.

Referring to FIG. 17d, proximally, the catheter is provided with a stationary pressure tight shaft seal 126 that fits in intimate, but relatively frictionless contact with a portion of the rotating drive shaft 162. The seal includes a ball seal 170 (available from Bal Seal Engineering Company, Inc., Foothill Ranch, Calif.), securely held in place by a seal holder 172 (stainless steel or elastomer), which abuts the distal end of the internal open area of the boot 122 and is held by compression of the ferrule assembly 164 (although other means of attachment such as injection molding are possible). The seal holder 172 includes a retainer sleeve 174 that extends coaxially with respect to the catheter 139. At the proximal end, within the ferrule, the drive shaft is held within a gland 178, preferably formed from hypotubing, which makes relatively frictionless contact with the ball seal 170, enabling rotation while preventing back flow of inflation fluid into the ferrule. The ball seal, as shown, is an annular U-shaped member, including within the U a canted coil spring 179 (such that the axis of each coil is tangent to the annulus) that presses the legs 175, 177 of the seal radially. The outer leg 175 of the seal engages an extension 176 of the seal holder, while the inner leg 177 of the seal engages the gland 178. The boot also includes a thin (few thousands of an inch) metal sleeve 171 for additional sealing around the catheter.

The drive shaft 162 is modified in the sealing area 168 by impregnating it with a thermoplastic material that fills the gaps in the individual wires to prevent flow of inflation fluid through the drive shaft inner lumen at typical inflation pressures of 100–120 psi or higher. Alternatively, the drive shaft may be sealed by impregnating it with a liquid that is hardenable, such as epoxy, and then covering that area with a section of cylindrical metal, such as hypotube, in order to form a smooth, fluid tight seal capable of holding up to typical balloon pressure. It will also be understood that other sealing members may be used, e.g. an O-ring.

Preparation of the device is accomplished by the following steps: A Leveen inflator is connected to the side arm. The side arm valve is opened and air is evacuated by suction. (Generally, the balloon contracts in a folded manner which leaves air passages through the interior of the balloon and prevents blockage of the passageway 151.) A hypodermic syringe fitted with a small gauge needle and filled with a fluid such as water or saline is then inserted through the distal tip septum seal. Fluid is introduced until surplus exits the side arm, at which point the valve is closed, reducing the chances that air will re-enter the catheter. Alternately, the fluid may be introduced via the side arm when an air venting needle is inserted into the distal septum.

The catheter is then attached to the driving motor, (not shown), by mating the ferrule 124 with a mateable receptacle which connects the ultrasound imaging electronics. Imaging can begin as soon as the deflated balloon is inserted into a subject lumen. Because the balloon material, saddle and sonolucent guide effectively transmit ultrasound energy, continuous imaging and monitoring of the subject lumen can be achieved.

By acoustic imaging, the device may be used to view 15 the lumen and stenoses for diagnostic purposes; then the balloon may be positioned accurately in any portion of the lumen such as a stenoses, and dilatation of the stenotic area may be performed using conventional dilatation technique while the progress of treatment is monitored by ultrasonic imaging and treatment is modified in response to the observed response of the tissue. Finally, after treatment, the balloon may be deflated and the lumen imaged to observe the treated site or view other sites.

The modular construction enables the ultrasound 25 imaging catheter's ability to be slidably inserted into a number of different types and styles of catheter sheaths. The pressure and fluid tight connector that is mounted distally to the location of the side arm connector enables various catheters, such as those with balloons of different sizes, to be effectively attached at the location of the side arm connector.

In operation, the acoustic imaging balloon catheter may be used to apply pressure (and optionally, heat) to dilate a blood vessel by molding the wall or an obstructing material (like plaque). The blood vessel may be a coronary artery, or a peripheral artery such as an iliac, femoral, renal, carotid, or popliteal artery. The balloon catheter may also be useful for dilatations in the biliary tract, esophagus or prostate. Referring to Table I below, preferred apparatus dimensions for various treatments are given.

TABLE I

| APPLICATION | DRIVESHAFT DIAMETER | CATHETER DIAMETER (BODY) | BALLOON DIAMETER (INFLATED) | BALLOON LENGTH | CATHETER LENGTH | EXTENSION LENGTH |
|---|---|---|---|---|---|---|
| Coronary Arteries | .025" | 3.0 F | 2–3 MM | 1.5 CM | 140 CM | .5 CM |
| Valvuloplasty | .054" | 6.2 F | 14 MM | 3 CM | 110 CM | 1.5 CM |
| Peripherals (e.g., iliacs, femorals) | .040" | 6.5 F | 7–8 MM | 4 CM | 95 CM | 1.5 CM |
| Extremities | .030" | 4.8 F | 4–6 MM | 3 CM | 95 CM | 1.5 CM |
| Esophagus and Prostate | .054" | 6.2 F | 30 MM | 4 CM | 95 CM | 1.5 CM |

Figure 18:
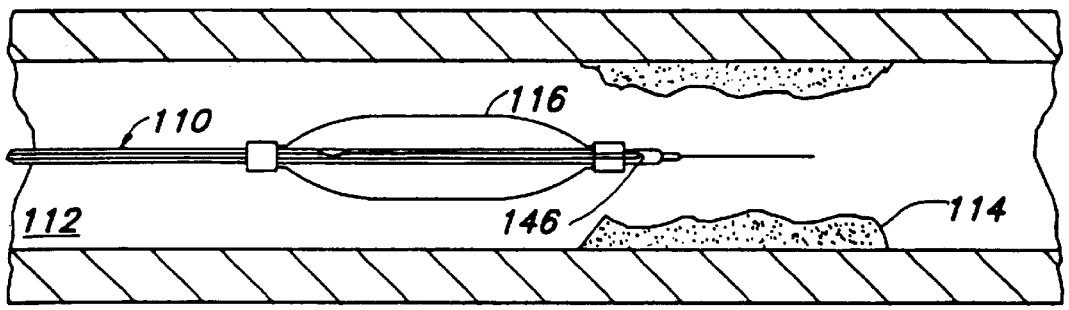
FIGS. 18–18e illustrate the use of an acoustic 30 imaging balloon angioplasty catheter in a blood vessel.

Referring to FIGS. 18–18d, illustrating dilatation of a blood vessel, a percutaneous insertion is made with a needle, and a guide wire is introduced into the blood vessel 11. The acoustic imaging balloon catheter no follows the wire (for example employing the saddle arrangement discussed above) and is positioned at an obstruction in the artery such as a plaque deposit 114 (FIG. 18) by visualizing the inner walls of the artery by acoustic imaging as the catheter is advanced.

Figure 18A:
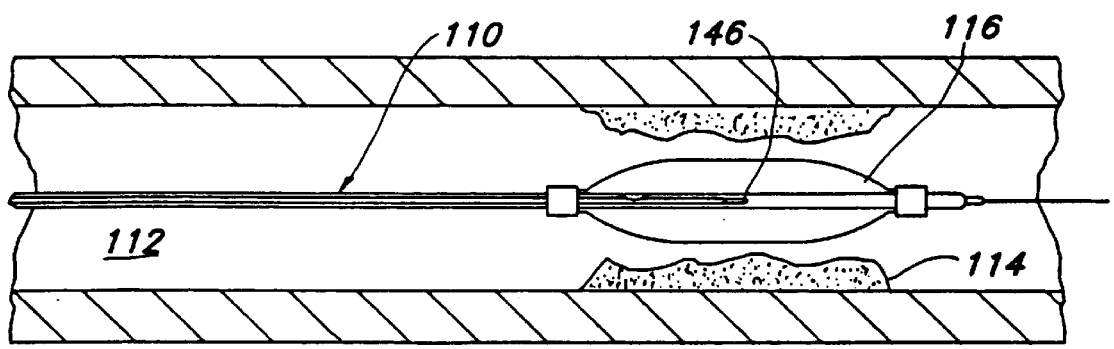

While imaging continues, the balloon 116 is inflated to engage the plaque material 114 forming the obstruction (FIG. 18a). As pressure and/or heat is applied to the occluding material, the operator views the progress of the dilatation to assure that the dilatation does not occur too rapidly, which may lead to the formation of cracks or flaps which may in turn lead to re-occlusion.

In the case of a heated balloon catheter, the pressure in the balloon may be kept below the normal pressure required under ambient conditions to widen the vessel to avoid cracking the plaque. Normal dilation pressure means the minimum pressure at which an unheated balloon causes substantial dilation of the respective lumen. The low, sub-dilatation pressure used initially to engage the plaque material may be, for example, about two atmospheres. In the case of angioplasty, normal dilation pressure is of the order of 5 to 10 atmospheres (varies with balloon size). The balloon self-forms around the irregular surfaces of the obstruction and provides a firm contact for efficient and even transfer of heat. As the occlusion yields (by virtue of heating and gentle pressure as described below), the balloon expands to maintain even contact with the surface. The operator monitors the dilatation by acoustic imaging to determine various physiological conditions and responses to treatment.

With the balloon inflated to a low level of pressure and engaging the obstruction, the user may initiate the bipolar heating between the electrodes 143, 144 as discussed above (e.g., by depressing a footswitch to start a heating program). Heat is dissipated into the fluid according to the formula $P=I^2R$. where P is the power that is dissipated into the fluid, I is the current that is passed through the electrodes, and R is the resistance of the fluid. The heat from the fluid is conducted across the balloon wall into the surrounding tissue 44. The fluid will heat to the temperature set by the user to carry out a temperature algorithm. The temperature at the balloon surface ranges from 45–90° C. and is typically from 50 to 70° C., sometimes preferably, around 60–65° C.

While heating, the operator monitors the condition and physiological response of the vessel under treatment by acoustic imaging. When the obstruction is under certain conditions of heat and pressure, the heterogeneous plaque material (usually including fat, fibrogen, calcium) softens, resulting in a change in the allowable volume of the balloon at a given low pressure (preferably below the pressure needed to crack the obstruction).

Figure 18B:
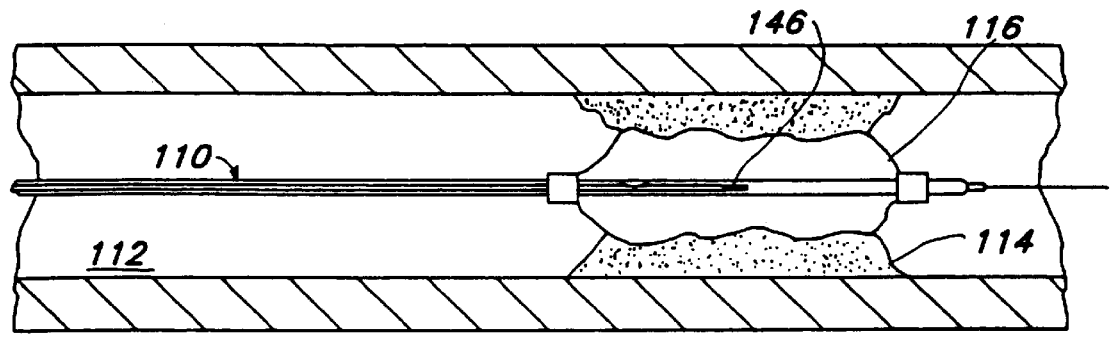

In FIG. 18b, for example, the stenoses is observed by acoustic imaging to expand slowly as the occluding material elastically (reversibly) expands with gentle heating until, upon reaching a yield point at time corresponding to the conditions of pressure and temperature at which the occlusion yields. Thereafter, the stenoses is observed by acoustic imaging to yield at a higher rate as the occluding material yields plastically (substantially non-reversibly).

Figure 18C:
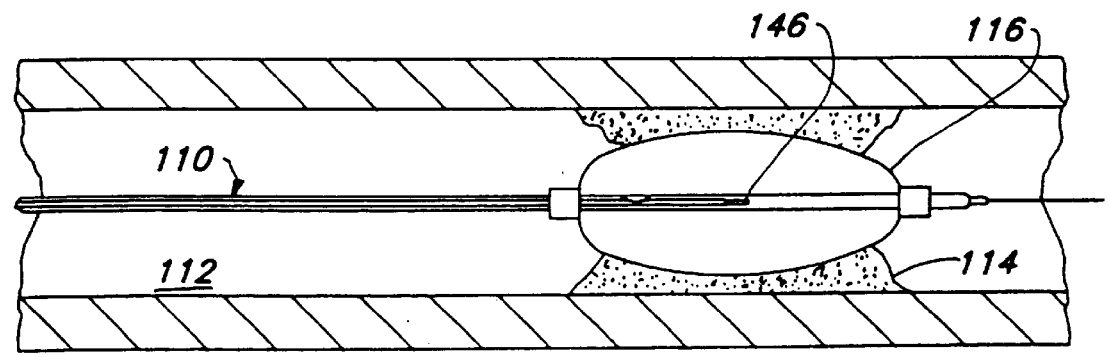

As shown in FIG. 18c, after observing the yield of the plaque by acoustic imaging, the operator determines the course of further treatment, which may include maintaining or slight changes in temperature or pressure of the balloon, to effect full dilatation of the artery where the continued treatment leads to full expansion of the balloon and artery at a time.

As illustrated in FIG. 18d after the vessel has been fully dilated, the temperature of the balloon is reduced, while the balloon remains inflated. Recycling, the temperature allows the material of the obstruction, the plaque, to be mold-formed by the balloon as it cools and reconstitutes. The interior walls of the remodeled lumen are left smooth and with reduced chance of re-occlusion 15. The temperature is reduced while the balloon is inflated.

Finally, as illustrated in FIG. 18e, the balloon is deflated and removed from the body lumen. The operator then can observe the dilated vessel by acoustic imaging.

Referring now to FIG. 19, in another embodiment of the acoustic imaging catheter device, the transducer 146 is positioned in the distal tip extension of the balloon catheter and distal to the balloon. A sonolucent window located distal to the, balloon allows imaging to take place during the positioning of the balloon and after treatment. In this case, ultrasonic energy is not transmitted through the catheter sheath 190, balloon 191 or saddle 192 as in the previously mentioned embodiments. After location and inspection of the area to be treated, the catheter is advanced a known amount, e.g. a few centimeters,(monitorable from outside the body) and the balloon is inflated. The dilatation is performed, and then the balloon is withdrawn, allowing a post dilatation view of the region.

In other embodiments, the transducer may be positioned proximal to the balloon. These embodiments may be particularly useful for prostate dilatation where the balloon is to be positioned distal to the urinary sphincter to avoid dilation of the sphincter. By visualizing the sphincter by acoustic imaging with a transducer proximal to the balloon, the operator is assured that the balloon is distal to the sphincter.

Referring now to FIGS. 20–20b, other embodiments of the acoustic imaging catheter device allow relative movement of the transducer and balloon so that the ultrasound transducer may be positioned in any longitudinal Position in the balloon, or distal or proximal to the balloon, for an assessment, inspection of the body lumen and monitoring of the placement of the balloon, the dilatation procedure and then post-treatment inspection. In FIG. 20, the drive shaft and transducer 146 may be slid axially as indicated by arrows 195 to move the transducer, for example, continuously to positions between position I, proximal to the balloon and position 11, distal to the balloon. A slide assembly 240 is provided including a housing 244 having a distal end which receives the catheter sheath 139 and drive shaft 145. The drive shaft contacts a pair of Oppositely arranged, relatively frictionless ball seals 245, 246 press fit within the housing against an inner body extension 249 and the distal end member 248 of the body which is threaded into the body 244. The ball seals engage a gland 250 as discussed with respect to FIG. 17d. The gland is attached to a thumb control 252, provided within the body to enable axial motion of the drive shaft to position the transducer within the catheter corresponding to regions within the balloon and in the distal extension, both of which are sonolucent. For example, it may be advantageous, as illustrated by the position of the transducer 146 in the series of FIGS. 18–18e, to position the transducer in the distal extension of the catheter during insertion of the catheter to inspect and locate the region to be treated by the balloon, then retract the transducer into a region corresponding to the balloon to observe dilatation and finally, the transducer may be slid forward for post treatment inspection of the lumen after balloon deflation.

The axially translatable transducer device further includes a carbon resistor 254 within the slide assembly housing, and contact means 258 attached to the thumb control and in contact with the resistor. Probe wires 256, 257 are connected to the resistor 254 and contact means 258 to provide variable resistance between the probe wires as the thumb control is slid axially, which is detected at detector 260, to provide monitoring of the axial position of the transducer. The thumb control may be hand actuated or controlled by automatic translator means 264 which receives 'control signals from a controller 266. In preferred embodiments, the output from the detector 260 is provided to an analysis means 268 which also receives the acoustic images from the transducer corresponding to various axial positions of the transducer within the catheter body to provide registry of the images with the axial transducer position on a screen 270. In preferred embodiments, the transducer is slid axially, along a continuous length or at selected positions of the catheter body, for example, from the balloon to the distal tip, and the analysis means includes storage means for storing images along the length to reconstruct a three-dimensional image of the lumen along the axial length of transducer travel.

FIG. 20b shows an embodiment wherein the catheter includes a bellows member 280 to enable axial motion of the catheter body with respect to the transducer.

In another embodiment of the acoustic imaging catheter device, the balloon is asymmetrical, either or both in shape and expansion capability, and is mounted on a catheter shaft that is torquable, and can then be positioned using acoustic imaging so that radially selective dilatation is accomplished on the desired portion of the lumen wall by torquing the catheter. As discussed above, the positioning, rupturing, stretching and compression of the lesion and surrounding tissue, and the deflation of the balloon can all be monitored with cross-sectional ultrasonic images.

For example, multiple balloons maybe used that are 15 for example, separately heated to effect asymmetric heating. The correct orientation of the balloons in the lumen can be achieved and confirmed by observation through acoustic imaging. Referring to FIGS. 21–22b a balloon catheter 200' comprises a catheter shaft 202 and at least two balloons 204 and 206. Catheter shaft 200 passes through the length of balloon 204. The proximal and distal ends of balloon 204 are tacked onto catheter shaft 202 at locations adjacent the proximal and distal ends of balloon 204. Catheter shaft 202 includes inflation and pressure equalization ports 207, 208 within balloon 204 through which fluid enters and exits balloon 204, and ports 210 and 212 through which fluid enters and exits balloon 206.

The fully extended diameter of each of the balloons 206 and 208, when inflated, typically ranges from 2 millimeters for vascular procedures to 20 to 35 millimeters for hyperthermia treatment of the prostate, esophagus or colon. The combined volume of the balloons ranges from ⅛ cc for the smallest balloons to 100 cc for the largest balloons. The wall thickness of the balloons 204 and 206 is about 0.001 inch. In some applications, e.g. where the catheter 200 is being used in a blood vessel, a guidewire 214, which can extend past the distal end of the catheter 5 may be used to guide the catheter through the vascular system or other luminal structures. The guidewire may also be passed through a saddle as discussed above, for example, with respect to FIG. 17a. The exteriors of the balloons are coated with a non-stick coating having a low coefficient or friction, such as silicone or polysiloxane. The non-heated balloon may be covered with a coat of heat-insulating material or silver heat-reflective material thereby enhancing the temperature difference between the heated balloon and the unheated balloon.

Balloons 204, 206 are fillable with an electrically conductive fluid such as normal saline (0.9 percent NaCl in water), a conductive radiopaque fluid, or a mixture of saline solution and a radiopaque fluid.

In an alternative construction of the embodiment 20 shown in FIGS. 21–21b, balloons 204 and 206 may be replaced by a single, multi-segmented balloon. Catheter shaft 202 passes through the length of one of the segments. The other segment connects with catheter shaft 10 at the locations of lumens 210 and 212.

Electrical contacts 218 and 220 which effect heating by RF power dissipation, as discussed above, are exposed to the fluid inside of one of the balloons 204, but are not substantially exposed to the fluid inside of the other balloon 206. Within the catheter 200 is positioned a coil-form drive shaft 222 (phantom) having at its distal portion an acoustic transducer 224. The shaft is rotatable, enabling acoustic imaging of the lumen to be treated for positioning of the catheter and balloons, monitoring treatment and post-treatment inspection of the lumen.

In FIG. 21a, the multiple balloon catheter is shown in cross-section along line B—B of FIG. 21. The catheter 202 includes a single lumen 230 which rotatably supports the drive shaft 222 as discussed above. Inflation fluid for both balloons is passed through the lumen 230 and the inflation ports 207, 208, 210 and 212 as described above. The location of the heater contacts 218, 220 in balloon 206 results in substantial heating of balloon 204, with only minor conduction of heat and RF power through the catheter body to balloon 206. Further details of a multiple balloon catheter adaptable to acoustic imaging are discussed in U.S. Pat. No. 5,151,100.

FIGS. 22 and 22a show sheath 12e, similar to sheath 12, which is addition ally fitted with an eyelet 90 through a solid portion of the tip to allow the free passage of a guide wire 92 which is used to help guide the catheter to a region of interest inside a passage of the body.

FIG. 23 shows sheath 12f having a two lumen construction. The large lumen contains the transducer and drive shaft while the small lumen contains a wire 94. As shown, wire 94 is a deflecting wire attached near the distal end, and is free to slide through its lumen under tension applied to ring 96 to cause the catheter to bend when pulled taut, thus providing a measure of control of the orientation of the distal end of the acoustic catheter while negotiating the passages of the body or the like. In another embodiment wire 94 may be a preformed stylet, which, when inserted through the second lumen, causes deflection of the tip.

FIG. 24 shows sheath 12g having a small hole 97 at its distal end to allow the passage of a fluid under pressure, such as saline or clot dissolving enzyme such as urokinase, or radiographic contrast enhancement fluids. By this device such fluids can be introduced under precise guidance using the ultrasound imaging capability of the catheter.

FIGS. 25 and 25a show sheath 12h placed in a specially designed hollow, rigid, sharply pointed metallic trocar 98 similar to a lance, designed to be driven into the body and further into the tissue of an organ of interest, such as the liver or spleen, to provide ultrasound imaging of an area where there is no natural passageway. A side-facing window 99 in the distal region of the trocar tube allows the passage of ultrasound energy from and to the transducer to enable imaging to take place. Alternatively, a portion of the trocar (phantom, FIG. 25a) may be formed of sonolucent material, to form an ultrasonic window. The hollow trocar tube serves further to prevent crushing or deformation of the ultrasound catheter under the considerable pressure required to drive the device into solid body tissue. After ultrasound inspection the imaging catheter may be withdrawn from this device and a biopsy device may then be inserted in its place with the advantage that the region from which the biopsy is to be taken has been very accurately located by acoustic imaging.

The acoustic imaging-trocar apparatus is useful, for example, for diagnosis of tumors in the liver. Typically liver cancer is first evidenced by a number of very small tumors that are diffuse and randomly located making them difficult to visualize by external ultrasound apparatus. By employing the acoustic imaging-trocar apparatus of the present invention early detection of cancerous tumors may be accomplished by driving the ultrasound catheter inside the trocar into the liver where small tumors are suspected or likely to be. By driving the catheter into the tissue, although there is no natural passageway, the operator can search for tumors in the field of view. When a tumor is found the operator can remove the ultrasound imaging catheter and place within the trocar a biopsy sampling instrument such as forceps 284 to collect a small portion of the tumor (FIG. 25b). The forceps jaws 283, 285 are moveable from proximal portions as indicated by arrows 287 to open and close the instrument to grasp a sample. Similar procedures may be carried out in the breast, in searching for small tumors. In general the benign tumors are more or less encapsulated whereas cancerous tumors have a diffuse edge therefore enabling a preliminary analysis of the tumor by acoustic imaging. In another embodiment, shown in FIG. 25c, the trocar may include at its distal end, in the vicinity of the transducer a radioactive pellet 286, for radiation treatment of tumors found by ultrasonic imaging.

FIG. 26 shows flexible, disposable sheath 12i made of integral, thin-walled extruded plastic which is more or less sonolucent. This construction avoids the necessity of having a separate dome or window attached to the distal end. The distal end is post formed (thinned, e.g. by drawing and blowing) after extrusion to provide the correct wall thickness dimension for best sonic transmission and mechanical strength and may be sealed fluid tight at the tip.

FIG. 27 shows sheath 12j which is similar to sheath 12i of FIG. 26, and additionally has an integral floppy tip made by continuing the drawing process to form a small diameter solid but flexible extension of the sheath beyond the sonolucent area; it can achieve certain of the advantages of catheter 12a of FIG. 13 but without the additional cost of adding a separate metal floppy guide wire.

Figure 28:
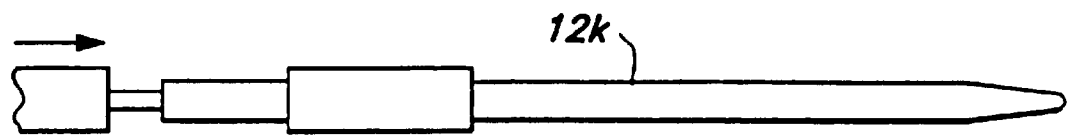
FIGS. 28 and 28a illustrate a thin-walled acoustic catheter sheath residing under tension during use.
Figure 28A:
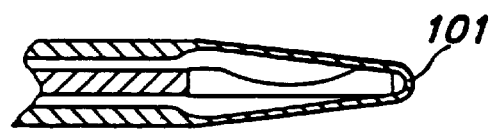

FIG. 28 shows sheath 12k which is formed to have an inner end bearing surface 101 at the distal tip for serving as an axial and radial bearing for the rotating ultrasound transducer. This bearing is, e.g., a small spherical or conical formation. By applying an axial, distal thrust on the shaft, and axial proximal tension on the catheter sheath, this bearing action creates tension on the tapered area of the dome, thus maintaining its shape by stretching, and allowing an even thinner material to be used, to reduce the loss acoustic energy in the substance of the window.

Figure 29:
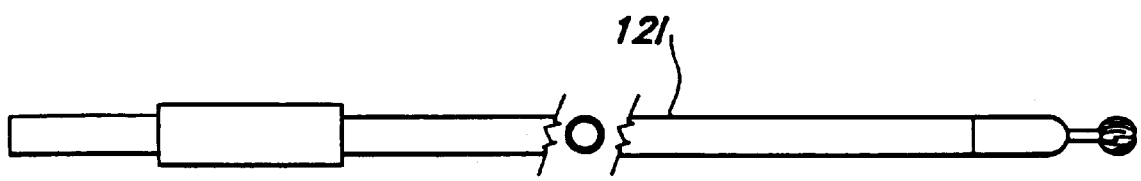
FIGS. 29 and 29a illustrate an acoustic catheter capable of driving a distal tool.
Figure 29A:
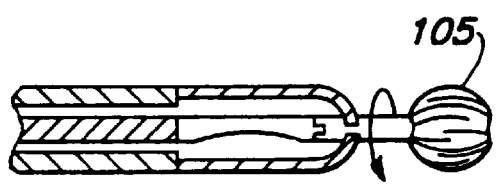

FIGS. 29 and 29a show sheath 121 which is fitted with a keyed rotating shaft that accepts the end of a similarly keyed ultrasound transducer, and acts as a power takeoff for driving a rotatable instrument such as the atherectomy cutter 105, shown.

Figure 30:
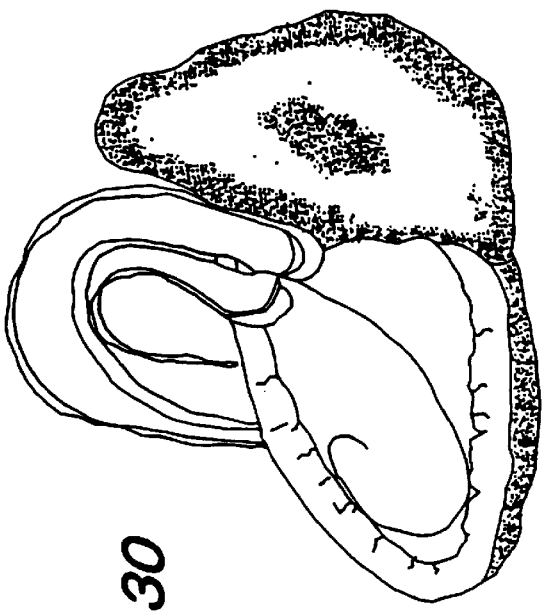
FIGS. 30 through 30c illustrate various positions of 25 an acoustic imaging catheter during imaging of a heart valve.
Figure 30A:
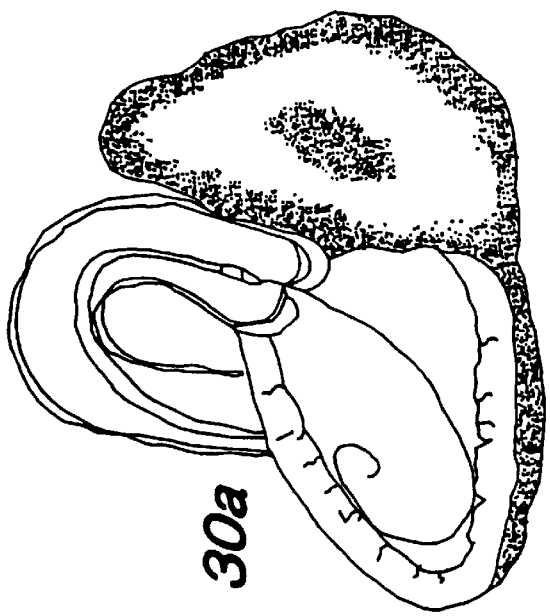
Figure 30B:
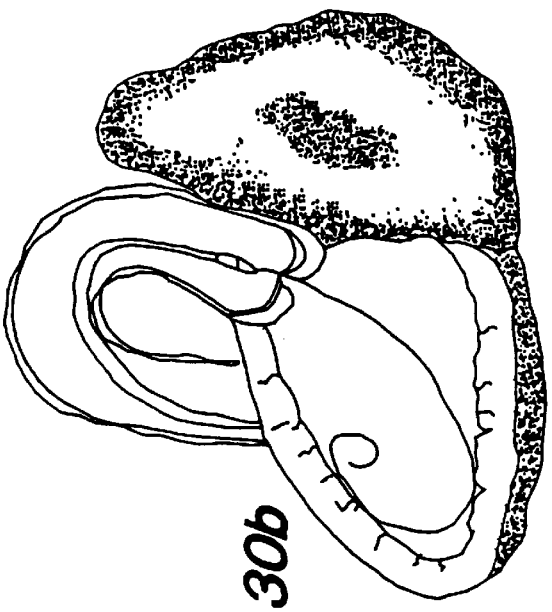
Figure 30C:
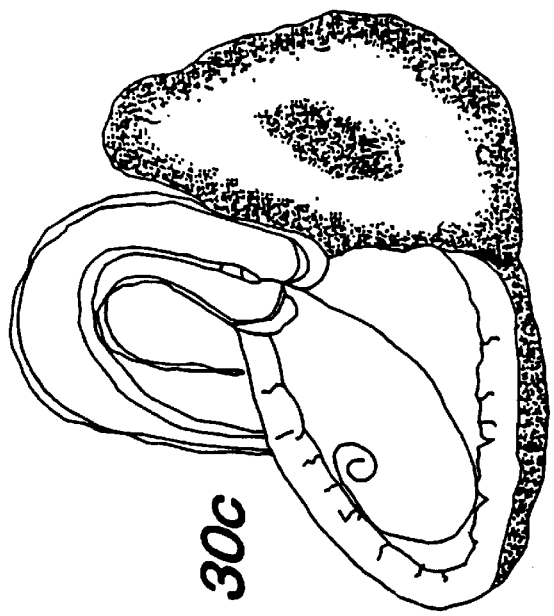

FIGS. 30–30c show a sheath constructed along the lines of sheath 12a of FIG. 13, being used in guiding and penetrating through the moving opening of a human heart valve. It shows how the floppy guiding wire acts as a stabilizer and a centering device allowing the ultrasound device to be moved forward and withdrawn repeatedly and consistently, as is desirable for proper imaging of the valve before and after valvuloplasty.

Figure 31:
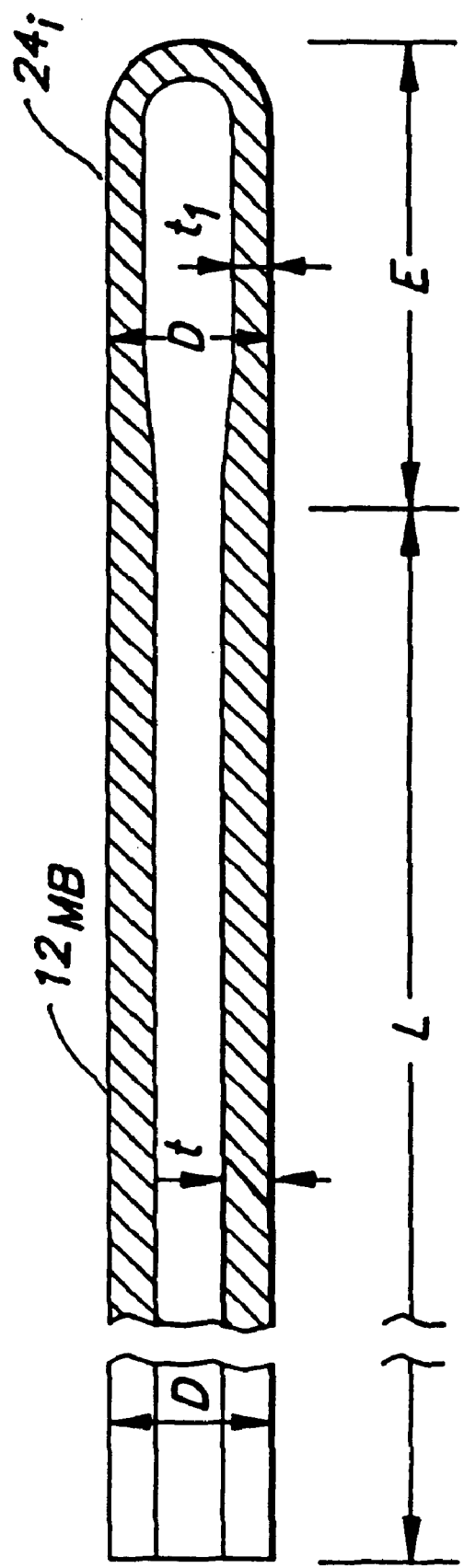
FIG. 31 illustrates an acoustic catheter sheath having an integrally formed acoustic window.

FIG. 31 shows an integrally-formed catheter sheath 25 having an acoustic window 24i originally of the same extruded material as the body of the catheter, the material of the window being modified to enhance its acoustic window properties. In this embodiment the main body $12_{mb}$ of the sheath has wall thickness t of 0.4 mm and outer diameter D of 2 mm. The integral window 24i has outer diameter D corresponding to that of the main body of the catheter and a modified wall thickness $t_1$ of 0.2 mm.

Any of these catheters may be additionally fitted with radiopaque markers either at the tip or the middle or both, designed to be visible when seen under the fluoroscope while intraluminal ultrasound imaging takes place. The markers are made of a metallic material that blocks X-ray radiation or a metal filled adhesive or epoxy is applied to the surface, in a groove, or at the end of the device. Additionally the metal-filled epoxy may be used to seal the end of the device as well as provide radiopacity.

Other embodiments are within the following claims.

What is claimed is:

1. An apparatus for detection of cancerous tumors in tissue having no natural passageway, comprising:

an imaging device supported on an end of a rotatable drive shaft, the imaging device adapted to transmit energy toward the tissue;

a fluid-confining sheath adapted to receive the imaging device; and a trocar adapted to receive the sheath, the trocar having a side-facing region adapted to maintain registry with the imaging device while the imaging device rotates, the side-facing region permitting the passage of the energy transmitted by the imaging device, enabling the imaging device to form images of tissue into which the trocar has been inserted.

2. The apparatus of claim 1 wherein the imaging device is removable from the trocar and the apparatus further includes a biopsy sampling device positionable in the trocar to sample tissue.

3. The apparatus of claim 2 wherein the biopsy sampling device is a forceps.

4. The apparatus of claim 1 wherein the trocar has a distal end, further comprising a radioactive pellet disposed within the distal end of the trocar for radiation treatment of a tumor found by ultrasonic imaging.

5. The apparatus of claim 1 wherein the imaging device includes an ultrasound transducer and the side-facing region is sonolucent.

6. The apparatus of claim 1 wherein the rotatable drive shaft is a rotatable coil-form drive shaft.

7. The medical device of claim 1 wherein the imaging device is removable from the trocar body.

8. A method for detection of cancerous tumors in tissue having no natural passageway, the method comprising:

providing an imaging device supported on the end of a rotatable drive shaft and a fluid-confining sheath adapted to receive the imaging device, in combination with a trocar adapted to receive the sheath, the trocar having a side-facing region permitting the passage of the energy transmitted by the imaging device, the side-facing region adapted to maintain registry with the imaging device while the imaging device rotates, enabling the imaging device to form images of tissue into which the trocar has been forced, and while observing images from the imaging device, advancing the imaging device into the tissue.

9. The method of claim 8, wherein the imaging device is removable from the trocar, and the method further comprises, at the position of a tumor:

removing the imaging device from the trocar, and introducing to the trocar a biopsy device to sample the tumor.

10. The method of claim 9, wherein the biopsy device includes a forceps.

11. The method of claim 8, wherein the tissue is a liver.

12. The method of claim 8, wherein the tissue is a breast.

13. The method of claim 8, wherein the rotatable drive shaft is a rotatable coil-form drive shaft.

14. The method of claim 8, wherein the imaging device includes an ultrasound transducer and the side-facing region is sonolucent.

15. A medical device for imaging body tissue having no natural passageway, the medical device comprising:

an elongated trocar body adapted to enter into the body tissue having no natural passageway;

an imaging device enclosed within the elongated trocar body, the imaging device constructed to transmit energy toward the body tissue;

a distal portion of the elongated trocar body comprising a material transparent to the energy transmitted by the imaging device toward the body tissue; and the imaging device being axially translatable relative to the distal portion of the elongated trocar body and having at least one axial position in which the energy from the imaging device passes through the distal portion of the elongated trocar body to the body tissue.

16. The medical device of claim 15, wherein the material of the distal portion of the elongated trocar body is optically transparent.

17. The medical device of claim 16, wherein the optically transparent material comprises high-impact polystyrene.

18. The medical device of claim 16, wherein the optically transparent material comprises polyethylene.

19. The medical device of claim 15, wherein the imaging device includes an ultrasound transducer and the material of the distal portion of the elongated trocar body is transparent to ultrasonic energy.

20. The medical device of claim 19, wherein the distal portion of the elongated trocar body is adapted to maintain registry with the imaging device while the imaging device rotates.

21. The medical device of claim 15, wherein the imaging device is mounted on the distal end of a drive shaft.

22. The medical device of claim 21, wherein the drive shaft is rotatable, so as to cause the imaging device to transmit energy in multiple radial directions toward the body tissue.

23. The medical device of claim 21, wherein the drive shaft is insertable into the trocar body prior to insertion of the elongated trocar body into the body of a living being, the imaging device being axially positionable relative to the distal portion of the elongated trocar body during insertion of the drive shaft into the elongated trocar body.

24. The medical device of claim 21, further comprising a drive shaft connector attached to the proximal end of the drive shaft, the drive shaft connector being configured to mate removably with another connector to engage electrically the imaging device with an imaging signal cable while simultaneously mechanically engaging the drive shaft with a motor device arranged to rotate the drive shaft.

25. The medical device of claim 15, wherein the imaging device is axially translatable relative to the distal portion of the elongate trocar body while the elongate trocar body is inside the body of a living being.

* * * * *